US011419899B2

(12) United States Patent
Saiki et al.

(10) Patent No.: US 11,419,899 B2
(45) Date of Patent: Aug. 23, 2022

(54) METHOD OF TREATING AORTIC ANEURYSM USING MUSE CELLS

(71) Applicants: TOHOKU UNIVERSITY, Sendai (JP); LIFE SCIENCE INSTITUTE, INC., Chiyoda-ku (JP)

(72) Inventors: Yoshikatsu Saiki, Sendai (JP); Mari Dezawa, Sendai (JP); Katsuhiro Hosoyama, Sendai (JP)

(73) Assignees: TOHOKU UNIVERSITY, Sendai (JP); LIFE SCIENCE INSTITUTE INC., Chiyoda-ku (JP)

(*) Notice: Subject to any disclaimer, the term of this patent is extended or adjusted under 35 U.S.C. 154(b) by 340 days.

(21) Appl. No.: 16/321,203

(22) PCT Filed: Jul. 28, 2017

(86) PCT No.: PCT/JP2017/027383
§ 371 (c)(1),
(2) Date: Jan. 28, 2019

(87) PCT Pub. No.: WO2018/021515
PCT Pub. Date: Feb. 1, 2018

(65) Prior Publication Data
US 2019/0175662 A1    Jun. 13, 2019

(30) Foreign Application Priority Data

Jul. 29, 2016   (JP) .............................. JP2016-150542

(51) Int. Cl.
| | | |
|---|---|---|
| *A01N 63/00* | (2020.01) | |
| *A61K 35/545* | (2015.01) | |
| *A61P 9/10* | (2006.01) | |
| *C12N 5/074* | (2010.01) | |
| *A61K 35/28* | (2015.01) | |
| *C12N 5/0735* | (2010.01) | |
| *C12N 5/0775* | (2010.01) | |

(52) U.S. Cl.
CPC ............ *A61K 35/545* (2013.01); *A61K 35/28* (2013.01); *A61P 9/10* (2018.01); *C12N 5/0606* (2013.01); *C12N 5/0607* (2013.01); *C12N 5/0663* (2013.01); *C12N 5/0665* (2013.01); *C12N 5/0668* (2013.01); *C12N 5/0696* (2013.01)

(58) Field of Classification Search
CPC .... A61K 35/545; A61K 35/28; C12N 5/0607; C12N 5/0606; C12N 5/0663; C12N 5/0665; C12N 5/0668; C12N 5/0696; A61P 9/10
USPC ....................................................... 424/93.1
See application file for complete search history.

(56) References Cited

U.S. PATENT DOCUMENTS

| | | | |
|---|---|---|---|
| 2002/0022055 A1* | 2/2002 | Signore .................... | A61K 9/06 424/486 |
| 2004/0161419 A1 | 8/2004 | Strom et al. | |
| 2011/0070647 A1 | 3/2011 | Dezawa et al. | |
| 2011/0117064 A1* | 5/2011 | Westenfelder ......... | C12Q 1/686 424/93.7 |
| 2016/0082048 A1 | 3/2016 | Yoshida et al. | |

FOREIGN PATENT DOCUMENTS

| | | | | |
|---|---|---|---|---|
| AU | 2013303492 B2 | | 2/2014 | |
| EP | 2 886 123 A1 | | 6/2015 | |
| JP | 5185443 B2 | | 4/2013 | |
| JP | 2015-159895 A | | 9/2015 | |
| JP | 201515985 | * | 9/2015 | |
| JP | 2015159895 | * | 9/2015 | |
| WO | WO-2011007900 A1 | * | 1/2011 | ................ A61P 9/00 |
| WO | WO 201 4/027684 A1 | | 2/2014 | |
| WO | WO-2014027684 A1 | * | 2/2014 | .......... C12N 5/0607 |
| WO | WO 2016/035419 A1 | | 3/2016 | |
| WO | WO 2016/044021 A1 | | 3/2016 | |

OTHER PUBLICATIONS

JP 2015159895 translation, 2015.*
Yamawaki-Ogata (Eur. J. Cardio-Thoracic Surgery, 2014, vol. 45, e156-165.*
Daugherty (J Clin Invest., 2000, vol. 105, No. 11, p. 1605-1612).*
Swaye (Circulation, 1983, vol. 67, No. 1, p. 134).*
Dezawa, WO 2011007900, Jan. 2011, translation.*
Schneider (Circulation, (Nov. 3, 2009) vol. 120, No. 18, Suppl. 2, pp. S1025).*
Extended European Search Report dated Jan. 28, 2020 in corresponding European Patent Application No. 17834517.9, 9 pages.
Katsuhiro Hosoyama et al., "Intravenously injected human multilineage-differentiating stress-enduring cells selectively engraft into mouse aortic aneurysms and attenuate dilatation by differentiating into multiple cell types", The Journal of Thoracic and Cardiovascular Surgery, Vo. 155, No. 6, XP085396862, Feb. 21, 2018, pp. 2301-2313 and 2313.e1-2313.e4.
International Search Report dated Sep. 26, 2017 in PCT/JP2017/027383, 1 page.

(Continued)

*Primary Examiner* — Michael C Wilson
(74) *Attorney, Agent, or Firm* — Oblon, McClelland, Maier & Neustadt, L.L.P.

(57) ABSTRACT

A cell product for prevention and/or treatment of vascular disorders such as aortic aneurysm, comprising a SSEA-3-positive pluripotent stem cell derived from a mesenchymal tissue in a living body or a cultured mesenchymal cell (Muse cell).

2 Claims, 15 Drawing Sheets

(56) References Cited

OTHER PUBLICATIONS

English translation of the International Preliminary Report on Patentability and Written Opinion of the International Searching Authority dated Feb. 7, 2019 in PCT/JP2017/027383 filed Jul. 28, 2017, 6 pages.
Aika Yamawaki-Ogata, et al., "Therapeutic Potential of Bone Marrow-Derived Mesenchymal Stem Cells in Formed Aortic Aneurysms of a Mouse Model" European Journal of Cardio Thoracic Surgery, vol. 45, No. 5, 2014, pp. e156-e165.
E. Petersen, et al., "Activity of Matrix Metalloproteinase-2 and -9 in Abdominal Aortic Aneurysms Relation to Size and Rupture" Eur, J. Vase. Endovasc. Surg. vol. 20, Nov. 2000, pp. 457-461.
Mathew Crowther, et al., "Increased Matrix Metalloproteinase 2 Expression in Vascular Smooth Muscle Cells Cultured from abdominal Aortic Aneurysms" Journal of Vascular Surgery, vol. 32, No. 3. Sep. 2000, pp. 575-583.
Tim Freestone, et al., "Inflammation and Matrix Metalloproteinases in the Enlarging Abdominal Aortic Aneurysm" Arteriosclerosis, Thrombosis and Vascular Biology, vol. 15, No. 8, Aug. 1995, pp. 1145-1151.
Oren Traub, et al., "Laminar Shear Stress Mechanisms by Which Endothelial Cells Transduce an Atheroprotective Force" Arterioscler Thromb Vase Biol. vol. 18, May 1998, pp. 677-685.
Robert Visse, et al., "Matrix Metalloproteinases and Tissue Inhibitors of Metalloproteinases Structure, Function, and Biochemistry" Circulation Research, vol. 92, May 2, 2003, pp. 827-839.
Monsurkazi, et al., "Influence of Intraluminal Thrombus on Structural and Cellular Composition of Abdominal Aortic Aneurysm Wall" Journal of Vascular Surgery. vol. 38, No. 6, Dec. 2003, pp. 1283-1292.
Vincent Fontaine, et al., "Role of Leukocyte Elastase in Preventing Cellular Re-Colonization of the Mural Thrombus" American Journal of Pathology, vol. 164, No. 6, Jun. 2004, pp. 2077-2087.
Eric Allaire, et al., "Vascular Smooth Muscle Cell Endovascular Therapy Stabilizes Already Developed Aneurysms in a Model of Aortic Injury Elicited by Inflammation and Proteolysis" Annals of Surgery, vol. 239, No. 3, Mar. 2004, pp. 417-427.
Jiang Xiong, et al., "Elastic Fibers Reconstructed Using Adenovirus-Mediated Expression of Tropoelastin and Tested in the Elastase Model of Abdominal Aortic Aneurysm in Rats" Journal of Vascular Surgery, vol. 48, No. 4, Oct. 2008, pp. 965-973.
Grégory Franck, et al. "Reestablishment of the Endothelial Lining by Endothelial Cell Therapy Stabilizes Experimental Abdominal Aortic Aneurysms" Circulation, vol. 127, May 7, 2013, pp. 1877-1887.
Noritoshi Nagaya, et al., "Intravenous Administration of Mesenchymal Stem Cells Improves Cardiac Function in Rats with Acute Myocardial Infarction through Angiogenesis and Myogenesis" Am. J. Physiol. Heart Circ. Physiol., vol. 287, No. 6, Dec. 2004, pp. H2670-H2676.
Noritoshi Nagaya, et al., "Transplantation of Mesenchymal Stem Cells Improves Cardiac Function in a Rat Model of Dilated Cardiomyopathy" Circulation, vol. 112, Aug. 23, 2005, pp. 1128-1135.
Kagiwada H., et al., "Human Mesenchymal Stem Cells as a Stable Source of VEGF-Producing Cells" J. Tissue Eng. Regen. Med. vol. 2, No. 4, Jun. 2008, pp. 184-189 (Abstract only).
F. Schneider., et al., "Bone Marrow Mesenchymal Stem Cells Stabilize Already-formed Aortic Aneurysms More Efficiently than Vascular Smooth Muscle Cells in a Rat Model" European Journal of Vascular and Endovascular Surgery, vol. 45, No. 6, Jun. 2013, pp. 666-672.
Ryotaro Hashizume, et al., "Mesenchymal Stem Cells Attenuate Angiotensin ll-Induced Aortic Aneurysm Growth in Apolipoprotein E-Deficient Mice" Journal of Vascular Surgery, vol. 54, No. 6, Dec. 2011, pp. 1743-1752.
Xian-Ming Fu, et al., "Intravenous Administration of Mesenchymal Stem Cells Prevents Angiotensin II-Induced Aortic Aneurysm Formation in Apolipoprotein E-Deficient Mouse" Journal of Translational Medicine, vol. 11, No. 175, 2013, 11 pages.
Yasumasa Kuroda, et al., "Unique Multipotent Cells in Adult Human Mesenchymal Cell Populations" PNAS, vol. 107, No. 19, May 11, 2010, pp. 8639-8643.
Shohei Wakao, et al., "Multilineage-Differentiating Stress-Enduring (Muse) Cells are a Primary Source of Induced Pluripotent Stem Cells in Human Fibroblasts" PNAS, vol. 108, No. 24, Jun. 14, 2011, pp. 9875-9880.
Yasumasa Kuroda, et al., "Isolation, Culture and Evaluation of Multilineage-Differentiating Stress-Enduring (Muse) Cells" Nature Protocols, vol. 8, No. 7, 2013, pp. 1391-1415.
Yamada, Y. et al., "Post-infarct administration of multilineage-differentiating stress-enduring (Muse) cells regenerates cardiomyocytes and microvessels and improves cardiac function and remodeling in rabbits", European Heart Journal, vol. 36, Supplement, Sep. 1, 2015, p. 946 Abstract P5444.
Yamada, Y. et al., "Multilineage-differentiating stress enduring (Muse) cells regenerate cardiomyocytes and microvessels and improve cardiac function and remodeling after myocardial infarction in rabbits", European Heart Journal, vol. 35, No. Supplement, Aug. 30, 2014, p. 112 Abstract P631.
Japanese Office Action dated Jul. 6, 2021 in Japanese Patent Application No. 20123-530413 (with English translation), 9 pages.
Aika Yamawaki-Ogata, et al., "Mesenchymal Stem Cells for Treatment of Aortic Aneurysms" World Journal Stem Cells, vol. 6, Issue 3, Jul. 26, 2014, pp. 278-287.
Takashi Muramatsu, et al., "Carbohydrate Markers of ES Cells" Trends in Glycoscience and Glycotechnology, vol. 21, No. 120, 2009, pp. 197-206.
Shoki Nishihara, "The Function of Glycan Structures Expressed on Embryonic Stem Cells" Trends in Glycoscience and Glycotechnology., vol. 21, No. 120, 2009, pp. 207-218.
Office Action dated Jul. 9, 2021. in U.S. Appl. No. 16/322,725, filed Feb. 1, 2019.

* cited by examiner

METHOD OF TREATING AORTIC ANEURYSM USING MUSE CELLS

TECHNICAL FIELD

The present invention relates to a cell product in regenerative therapy. More particularly, the present invention relates to a cell product comprising a pluripotent stem cell effective in repairing and regenerating damaged blood vessels.

BACKGROUND ART

Aneurysm is a pathology in which a weakened portion of an artery wall is swollen, and includes true aneurysm in which an artery expands while maintaining the three-layer structure comprising tunica intima, tunica media, and tunica adventitia, and dissecting aneurysm in which an artery expands after a tear in the tunica media in the arterial wall occurs and causes an artery dissection. These disorders can be a direct cause of death. In particular, aortic aneurysm has been considered for many years to be caused by vessel wall disorders due to arteriosclerosis and hypertension. However, from recent studies, it is now considered to be also caused by inflammation, oxidative stress and the like occurring in a vascular wall, especially in a tunica media and a tunica adventitia (e.g., Non-Patent Documents 1 to 3).

Due to the above causes, inflammatory cells, mainly lymphocytes and monocytes/macrophages, infiltrate into the artery wall, activating various proteases such as matrix metalloproteinases (MMPs), resulting in decomposition and disruption of extracellular matrix composed of elastin fibers and collagen fibers in tunica media and tunica adventitia. Simultaneously, thinning and weakening of the aortic wall such as due to reduction and dysfunction of vascular endothelial cells or apoptosis of smooth muscle cells also occur. It is considered that these lead to irreversible enlargement of the artery and aneurysm formation (e.g., Non-Patent Documents 4 to 7).

Regarding the occurrence of aortic dissection, arterial wall degradation due to arteriosclerosis and hypertension causes tearing of the tunica intima in the arterial wall, which result in blood inflow into the tear, causing dissociation into two lumens, true lumen and false lumen, at the level of the tunica media. In the chronic phase, the fragility of the aortic wall and various risk factors of the arteriosclerosis as the backgrounds thereof lead to aneurysm formation in many cases.

Aortic aneurysm does not show any symptoms until arterial rupture or dissection occurs, but it is often found in periodic health examinations or health checkups and diagnostic imaging performed for other purposes. In general, when the diameter of the aortic aneurysm is about 5 cm or more, treatment such as surgical artificial vessel replacement or aortic stent-grafting (a method of inserting a folding graft from a small incision in the groin to the aorta) is performed in order to repair the aneurysm.

However, it is difficult to detect true aneurysms and dissecting aneurysms in an early stage. In addition, aortic aneurysms rarely rupture when the diameter is less than about 5 centimeters. Thus, in such an early stage, only preventive treatment to reduce the risk of progression or rupture of the aneurysm, such as lowering the heart rate and blood pressure using an antihypertensive agent and smoking cessation, has been done.

Therefore, there remains a need in fundamental therapy for true aneurysm and dissecting aneurysm, as well as vascular disorders leading thereto in earlier stages, such as revascularization.

Recently, for the purpose of complete cure of aortic aneurysms by revascularization, treatment of aneurysms with various cells has been employed. For example, intravascular treatment with vascular smooth muscle cells in a rat xenograft model disclosed in Non-Patent Document 8 showed an effect of shrinking the aneurysm in 8 weeks after the treatment via catheter. Treatment with an adenovirus vector containing a recombinant tropoelastin gene in a rat elastase model disclosed in Non-Patent Document 9 also showed a reduction in the aneurysm size accompanying an increase of elastin fiber. Furthermore, treatment with endothelial cells in a rat xenograft model disclosed in Non-Patent Document 10 showed an effect of shrinking the aneurysm in 8 weeks after the treatment via catheter. However, all of the treatments are based on vascular cell transplantation or gene therapy, and furthermore the effects are insufficient.

Recently, it has been found that mesenchymal stem cells (MSCs) having self-proliferating and multipotential abilities not only differentiate into vascular endothelial cells but also secrete vascular endothelial growth factor (VEGF) (e.g., Non-Patent Documents 11 to 13). Thus, treatment of aneurysms by regenerative therapy using MSCs has also been attempted (e.g., Non-Patent Documents 14 to 17). However, the therapeutic effect by regenerative therapy using MSC for aneurysms is not yet sufficient. There remains a particular need for a method of fundamentally preventing and treating aneurysms through revascularization, comprising administering a small dose of MSCs, and allowing the MSCs to invade, for example, into the vascular media at an injured site, adhere thereon, and differentiate into vascular cells at the injured site, is particularly needed.

Studies by Dezawa, one of the present inventors, has revealed that pluripotent stem cells that are present in mesenchymal cell fractions (Multilineage-differentiating Stress Enduring cells; Muse cell), can be obtained without gene introduction or induction by cytokines or the like, and express SSEA-3 (Stage-Specific Embryonic Antigen-3) as a surface antigen can be responsible for the pluripotency possessed by the mesenchymal cell fractions, and applied to disease treatment aimed at tissue regeneration (e.g., Patent Document 1; and Non-Patent Documents 18 to 20). However, it has not been demonstrated whether use of Muse cells in prevention and/or treatment of vascular disorder could provide the expected therapeutic effects.

PRIOR ART REFERENCES

Patent Documents

Patent Document 1: Japanese Patent No. 5185443

NON-PATENT DOCUMENTS

Non-Patent Document 1: Petersen E, et al. J Vasc Endovasc Surg 2000: 457-461.

Non-Patent Document 2: Crowther M, et al. J Vasc Surg 2000: 575-583.

Non-Patent Document 3: Freestone T, et al. Arterioscler Thromb Vasc Biol 1995: 1145-1151.

Non-Patent Document 4: Traub O, et al. Arterioscler Thromb Vasc Biol 1998: 677-685.

Non-Patent Document 5: Visse R, et al. Circ Res 2003: 827-39.

Non-Patent Document 6: Kazi M, et al. J Vasc Surg 2003: 1283-1292.

Non-Patent Document 7: Fontain V, et al. Am J Pathol 2004: 2077-2087.

Non-Patent Document 8: Allaire E, et al. Annals of Surgery 2004: 239(3): 417-427.

Non-Patent Document 9: Xiong J, et al. J Vasc Surg 2008: 48(4): 965-973

Non-Patent Document 10: Franck G, et al. Circulation 2013: 127: 1877-1887

Non-Patent Document 11: Nagaya, N, et. al. Am J Physiol Heart Circ Physiol, 2004: 287(6), 2670-2676.

Non-Patent Document 12: Nagaya N, et. al. Circulation, 2005: 112, 1128-1135.

Non-Patent Document 13: Kagiwada H, et. al. J Tissue Eng Regen Med, 2008: 2(4), 184-189.

Non-Patent Document 14: Schneider F, et al. Eur J Vasc Endovasc Surg, 2013: 45(6): 666-672

Non-Patent Document 15: Hashizume R, et al. J Vasc Surg, 2011: 54(6): 1743-1752

Non-Patent Document 16: Fu X M, et al. J Transl Med, 2013: 11: 175.

Non-Patent Document 17: Yamawaki A, et al. Eur J Cardiothorac Surg, 2014: 45(5): e156-165.

Non-Patent Document 18: Kuroda Y et al. Proc Natl Acad Sci USA, 2010: 107: 8639-8643.

Non-Patent Document 19: Wakao S et al. Proc Natl Acad Sci USA, 2011: 108: 9875-9880.

Non-Patent Document 20: Kuroda Y et al. Nat Protc, 2013: 8: 1391-1415.

SUMMARY OF THE INVENTION

Problems to be Solved by the Invention

An object of the present invention is to provide a cell product for prevention and/or treatment of vascular disorders.

Means for Solving the Problems

The present inventors have found that: in a vascular disorder model using an immunodeficient mouse that does not reject human cells, human Muse cells that are administered via a blood vessel or the like, or administered directly to the injured vascular site of the subject and its surroundings, accumulated in and engrafted to, and then restored and repaired the injured blood vessel, resulting in amelioration of or recovery from the vascular disorder; and thus that the Muse cells can be suitably used in treatment and prevention of vascular disorders including aortic aneurysm, thereby completed the present invention.

Accordingly, the present invention provides the following [1] to [11].

[1] A cell product for prevention and/or treatment of a vascular disorder, comprising a SSEA-3-positive pluripotent stem cell derived from a mesenchymal tissue in a living body or a cultured mesenchymal cell.

[2] The cell product of item [1], wherein the vascular disorder is aneurysm.

[3] The cell product of item [2], wherein the aneurysm is aortic aneurysm.

[4] The cell product of item [3], wherein the aortic aneurysm is abdominal aortic aneurysm or thoracic aortic aneurysm.

[5] The cell product of item [2], wherein the aneurysm is visceral aneurysm, peripheral artery aneurysm, cerebral aneurysm or coronary artery aneurysm.

[6] The cell product of item [2], wherein the aneurysm is fusiform aneurysm or saccular aneurysm.

[7] The cell product of item [2], wherein the aneurysm is true aneurysm, dissecting aneurysm or false aneurysm.

[8] The cell product of item [2], wherein the aneurysm is arteriosclerotic aneurysm, inflammatory aneurysm or infected aneurysm.

[9] The cell product of any one of items [1] to [8], wherein said pluripotent stem cell is one having all of the following characteristics:
(i) having low or no telomerase activity;
(ii) capable of differentiating into any of tridermic cells;
(iii) showing no neoplastic proliferation; and
(iv) having self-renewal capacities.

[10] A method of preventing and/or treating a vascular disorder, comprising a step of administering an effective amount of SSEA-3-positive pluripotent stem cells derived from a mesenchymal tissue in a living body or a cultured mesenchymal cell to a subject in need thereof.

[11] A cell product for use in prevention and/or treatment of a vascular disorder, comprising a SSEA-3-positive pluripotent stem cell derived from a mesenchymal tissue in a living body or a cultured mesenchymal cell.

Effects of the Invention

In the present invention, when Muse cells are administered to a subject with a vascular disorder via a blood vessel or the like, or directly to its injured vascular site and its surroundings, the cells can restore and repair the injured blood vessel, resulting in improvement or recovery of functions during the vascular disorder. The cell product of the present invention can exert its effect not only during the acute phase of vascular disorder, but also during the chronic phase, thereby sustaining the therapeutic effect over a long period of time.

Since Muse cells can efficiently migrate and engraft to injured blood vessels, and then spontaneously differentiate into constituent cells such as vascular cells at the engraftment site, they do not require differentiation induction into therapeutic target cells prior to transplantation. In addition, Muse cells are non-tumorigenic and superior in safety. Furthermore, since Muse cells are not exposed to immune rejection, treatment with allogenic preparations produced from donors is also possible. Therefore, the Muse cells having the superior abilities as described above can provide easy and feasible means for treatment of patients with vascular disorders.

BRIEF DESCRIPTION OF THE DRAWINGS

FIG. 6 also shows a graph showing the numbers of aSMA/GFP double-positive cells per unit area of the indicated groups after 3 weeks and 8 weeks (bottom).

FIG. 7 also shows a graph showing the numbers of CD31/GFP double-positive cells per unit area of the indicated groups after 3 weeks and 8 weeks (bottom).

FIG. 8 also shows a graph showing the numbers of F4/80 double-positive cells per unit area of the indicated groups after 3 weeks and 8 weeks (bottom).

FIG. 9 also shows a graph showing the percentages of Ki67-positive cells of the Muse cell-treated groups after 3 weeks and 8 weeks (bottom).

DETAILED DESCRIPTION OF THE INVENTION

Figure 1:
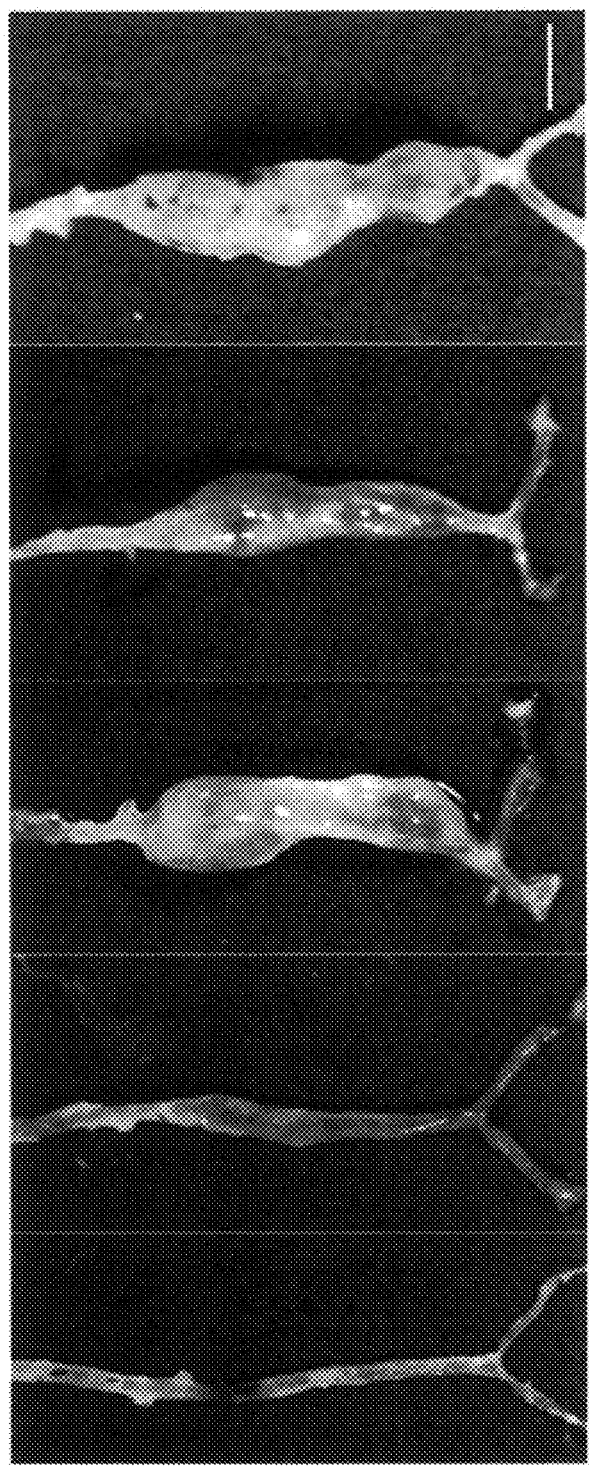
FIG. 1 shows photographs of aortic aneurysms removed from mice of the indicated groups after 8 weeks. The scale bar represents 3 mm.

The present invention relates to a cell product for prevention and/or treatment of vascular disorders, the cell product comprising a SSEA-3-positive pluripotent stem cell (Muse cell). The present invention will be described in detail below.

1. Indications

The cell product of the present invention comprising a SSEA-3-positive pluripotent stem cell (Muse cell) is used for prevention and/or treatment of vascular disorders. As used herein, the term "vascular disorder" includes blood vessel disorders caused by arteriosclerosis or hypertension, or by inflammation, oxidative stress or the like occurring in vascular wall, particularly in tunica media and tunica adventitia; as well as in rare cases blood vessel disorders caused by puncture wounds, bacterial or fungal infections on arterial wall, or the like. Specific example of the vascular disorder includes aneurysm in which weakened part of arterial walls bulges due to vascular disorders.

As used herein, the term "vascular disorder," which means arterial wall weakening due to the above-mentioned causes resulting in aneurysm, also includes blood vessel disorders at initial stage before reaching aneurysm. In the present invention, aneurysms include: thoracic aortic aneurysm, abdominal aortic aneurysm, visceral aneurysm, peripheral artery aneurysm, cerebral aneurysm, and coronary artery aneurysm according to classification based on the site of occurrence; fusiform aneurysm, and saccular aneurysm according to classification based on the shape; true aneurysm, dissecting aneurysm, and false aneurysm according to classification based on the state of the vascular wall; and arteriosclerotic aneurysm, inflammatory aneurysm, and infected aneurysm according to classification based on the cause.

2. Cell Product (1) Pluripotent Stem Cell (Muse Cell)

The pluripotent stem cell used in the cell product of the present invention is a cell that was found in human living body and named "Muse (Multilineage-differentiating Stress Enduring) cell" discovered by Dezawa, one of the present inventors. It is known that Muse cells can be obtained from, for example, bone marrow aspirate, adipose tissue (Ogura, F., et al., Stem Cells Dev., Nov. 20, 2013 (Epub) (published on Jan. 17, 2014)) and dermal connective tissue of skin, and are broadly present in tissues and connective tissues in organs. This cell also has both characteristics of pluripotent stem cell and mesenchymal stem cell and is identified as, for example, a cell positive for "SSEA-3 (Stage-specific embryonic antigen-3)," a cell surface marker, preferably as a double-positive cell that is positive for SSEA-3 and CD-105. Therefore, Muse cells or a cell fraction containing Muse cells can be isolated from living tissues using, for example, expression of SSEA-3 only or a combination of SSEA-3 and CD-105 as cell surface marker. Methods for separation and identification of, and characteristics of Muse cell have been specifically disclosed in WO2011/007900. Muse cells can also be selectively enriched by utilizing the high resistance of Muse cells to various external stresses and culturing under various external stress conditions, such as under protease treatment, under hypoxic condition, under low-phosphate condition, in a low serum concentration, under low-nutrition condition, under heat shock exposure, in the presence of toxic substance, in the presence of reactive oxygen species, under mechanical stimulation, and under pressure treatment. As used herein, the pluripotent stem cells (Muse cells) or a cell fraction containing Muse cells prepared, as a cell product for treating vascular disorders, from mesenchymal tissues or cultured mesenchymal tissues using SSEA-3 as cell surface marker may be simply referred to as "SSEA-3-positive cells." As used herein, the term "non-Muse cells" may refer to cells contained in mesenchymal tissues or cultured mesenchymal cells and excluding "SSEA-3-positive cells."

Muse cells or a cell fraction containing Muse cells can be prepared from living tissues (e.g., mesenchymal tissues) using cell surface markers, SSEA-3 or SSEA-3 and CD-105, as cell surface marker. As used herein, the term "living" means mammal living body. In the present invention, the living body does not include fertilized egg and embryos in developmental stages before blastocyst stage, but includes embryos in developmental stages of blastocyst stage or later, including fetus and blastula. Examples of the mammal include, but not limited to, primates such as human and monkey; rodents such as mouse, rat, rabbit, and guinea pig; and cat, dog, sheep, pig, cattle, horse, donkey, goat, and ferret. The Muse cell used in the cell product of the present invention is definitively distinguished from embryonic stem cells (ES cells) and iPS cells in that the Muse cell are directly isolated with markers from living tissues. The term "mesenchymal tissue" refers to tissues present in tissues or various organs such as bone, synovial membrane, fat, blood, bone marrow, skeletal muscle, dermis, ligament, tendon, dental pulp, umbilical cord, cord blood, and amnion. The Muse cells can be obtained from, for example, bone marrow, skin, adipose tissue, blood, dental pulp, umbilical cord, cord blood, and amnion. Preferably, a mesenchymal tissue of the living body is collected, and then Muse cells are prepared from the tissue and used. Alternatively, using the preparation method described above, the Muse cells may be prepared from cultured mesenchymal cells such as fibroblast and bone marrow mesenchymal stem cell.

The cell fraction containing Muse cells used in the cell product of the present invention can also be prepared by a method comprising exposure of mesenchymal tissues of the living body or cultured mesenchymal cells to an external stress in order to selectively allow stress-tolerant cells to proliferate and collection of the cells with the increased abundance ratio of stress-tolerant cells.

Above-mentioned external stress may be any of the following: protease treatment, culture under hypoxia, culture under low-phosphate condition, culture under low serum concentration, culture undernutrition condition, culture under heat shock exposure, culture at low temperatures, freezing treatment, culture in the presence of toxic substances, culture in the presence of reactive oxygen species, culture under mechanical stress, culture under shaking, culture under pressure treatment or physical shocks, or combination thereof.

Above-mentioned protease treatment is preferably carried out for 0.5 to 36 hours in total to exert the external stress. The concentration of the protease may be a concentration used when cells adhered to a culture vessel areharvested, when cell aggregates are separated into single cells, or when single cells are collected from a tissue.

Preferably, Above-mentioned protease is serine protease, aspartic protease, cysteine protease, metalloprotease, glutamic protease or N-terminal threonine protease. More preferably, Above-mentioned protease is trypsin, collagenase or Dispase.

The Muse cell used in the cell product of the present invention may be autologous or allogeneic to a recipient of cell transplantation.

As described above, Muse cells or a cell fraction containing Muse cells can be prepared from tissues of the living body, for example, by using SSEA-3-positivity or SSEA-3 and CD-105-double-positivity as cell surface marker. Human adult skin is known to comprise various types of stem cells and precursor cells. However, Muse cell is different from these cells. These stem cells and precursor cells include skin-derived precursor cell (SKP), neural crest stem cell (NCSC), melanoblast (MB), pericyte (PC), endothelial precursor cell (EP), and adipose-derived stem cell (ADSC). Muse cells can be prepared using "non-expression" of markers unique to these cells as cell surface marker. More specifically, Muse cells can be isolated using as an index of negative expression for at least one, e.g., 2, 3, 4, 5, 6, 7, 8, 9, 10 or 11, of 11 cell surface markers selected from the group consisting of CD34 (a marker for EP and ADSC), CD117 (c-kit) (a marker for MB), CD146 (a marker for PC and ADSC), CD271 (NGFR) (a marker for NCSC), NG2 (a marker for PC), vWF factor (von Willebrand factor) (a marker for EP), Sox10 (a marker for NCSC), Snail (a marker for SKP), Slug (a marker for SKP), Tyrp1 (a marker for MB), and Dct (a marker for MB). Muse cells can be prepared by using as an index of negative expression for, for example, but not limited to, CD117 and CD146; CD117, CD146, NG2, CD34, vWF and CD271; or the above-described 11 markers.

The Muse cell having the above-described characteristics and used in the cell product of the present invention also has at least one selected from the group consisting of the following characteristics:

(i) having low or no telomerase activity;
(ii) capable of differentiating into any of tridermic cells;
(iii) showing no neoplastic proliferation; and
(iv) having self-renewal capacities.

Preferably, the Muse cell used in the cell product of the present invention has all of the characteristics described above. With respect to (i) above, the phrase "having low or no telomerase activity" means that the telomerase activity is low or undetectable when detected using, for example, TRAPEZE XL telomerase detection kit (Millipore). Having "low" telomerase activity means, for example, having a telomerase activity comparable to somatic human fibroblast, or having 1/5 or less telomerase activity, preferably one-tenth or less telomerase activity, as compared with that of HeLa cell. With respect to (ii) above, the Muse cell is capable of differentiating into triploblastic cells (endodermal, mesodermal, and ectodermal cells) in vitro and in vivo. For example, the Muse cell can differentiate into hepatocyte (including cells expressing hepatoblast markers or hepatocyte markers), neuron, skeletal muscle cell, smooth muscle cell, osteocyte, or adipocyte by in vitro culture for induction. The Muse cell may also be able to differentiate into triploblastic cells when it is transplanted in testis in vivo. Further, the Muse cell is capable of migration and engraftment into injured organs (such as heart, skin, spinal cord, liver, and muscle) and differentiation into cells suitable for the tissues when transplanted to a living body via intravenous injection. With respect to (iii) above, the Muse cells can proliferate from single cell at a growth rate of about 1.3 days in suspension culture and form cell clusters similar to embryoid body at a certain size and then arrest their proliferation after about 14 days. When these cell clusters similar to embryoid body are transferred to adherent culture, the cells restart proliferation and cells proliferated from the cell clusters spread at a growth rate of about 1.3 days. Further, the cells are characterized in that, when transplanted into testis, they do not become cancerous for at least half a year.

With respect to (iv) above, the Muse cell has self-renewal (self-replication) capacities. The term "self-renewal" means that differentiation into three-germ layer cells from cells contained in the first cell clusters similar to embryoid-body derived by single Muse cell in a suspension culture can be observed; that formation of the second-generation of embryoid-body-like clusters by again culturing single cell of the first-generation of embryoid-body-like clusters in a suspension culture can be observed; and that differentiation into three-germ layer cells and formation of the third-generation of embryoid-body-like clusters obtained by single-cell suspension culture derived from the second-generation of embryoid-body-like clusters can be observed. Self-renewal means to be able to repeat for one or more above-mentioned experimental cycles.

(2) Preparation and Use of Cell product

The method of obtaining the cell product of the present invention include, but not limited to, suspending Muse cells or a cell fraction containing Muse cells obtained in (1) above in a physiologic saline or a suitable buffer solution (e.g., phosphate buffered saline). In this case, if only small numbers of Muse cells are obtained from an autologous or allogeneic tissue, these cells may be cultured before cell transplantation until the fixed number of cells is obtained. As previously reported (WO2011/007900), since Muse cells do not become tumorigenic, if cells collected from a living tissue and some undifferentiated cells remain, they have low possibility of converting to malignant cells and thus are safe. The collected Muse cells can be cultured in any common culture medium (e.g., α-minimum essential medium (α-MEM) supplemented by 10% calf serum). More specifically, with reference to the above-described WO2011/007900, for example, a culture medium, and additives (e.g., antibiotics, and serum) are appropriately selected for culture and proliferation of Muse cells, so that a solution containing the fixed concentration of Muse cells can be prepared. When the cell product of the present invention is administered to human subject, bone marrow aspirates are collected from a human ilium, and then, for example, bone marrow mesenchymal stem cells are cultured to obtain as adherent cells from the bone marrow aspirate and proliferated until reaching the cell amount where a therapeutically effective amount of Muse cells can be obtained. Thereafter, Muse cells are sorted using an antigenic marker SSEA-3 as cell surface marker. These autologous or allogeneic Muse cells can be used for preparing the cell product. Alternatively, for example, bone marrow mesenchymal stem cells obtained from the bone marrow aspirates are cultured under external stress conditions to proliferate and enrich Muse cells until they reach a therapeutically effective amount. Then, these autologous or allogeneic Muse cells can be used for preparing the cell product.

When the Muse cells are used in the cell product, the cell product may contain dimethyl sulfoxide (DMSO), serum albumin or the like for protection of the cells and antibiotics or the like for prevention of contamination and proliferation of bacteria. The cell product may further contain other pharmaceutically acceptable components (e.g., carrier, excipient, disintegrant, buffer agent, emulsifier, suspending agent, soothing agent, stabilizer, preservative, antiseptic, physiologic saline). These agents and drugs can be added to the cell product in an appropriate concentration by the skilled person. Thus, Muse cells can also be used as a pharmaceutical composition containing various additives.

The number of Muse cells contained in the cell product prepared above can be appropriately adjusted to obtain desired effects in treatment of vascular disorders, in consideration of, for example, sex, age, and weight of subjects, condition of diseased part, and condition of cells to be used. Individuals to be the subject includes, but not limited to, mammals such as human. The cell product of the present invention may be administered multiple times (e.g., 2 to 10 times) at appropriate intervals (e.g., twice a day, once a day, twice a week, once a week, once every two weeks, once a month, once every two months, once every three months, or once every six months) until a desired therapeutic effect is obtained. Thus, depending on the condition of the subject, the therapeutically effective amount preferably is a dosage of, for example, $1\times10^3$ to $1\times10^{10}$ cells/individual/dose in 1 to 10 doses. Examples of total dosage for an individual include, but not limited to, $1\times10^3$ to $1\times10^{11}$ cells, preferably $1\times10^4$ to $1\times10^{10}$ cells, more preferably $1\times10^5$ to $1\times10^9$ cells.

The Muse cell used in the cell product of the present invention is characterized by migration and engraftment to injured organs. Thus, in regard to the administration of the cell product, the administration route of the cell product, and the type of the blood vessel into which the cell product is administered (vein or artery) are not limited.

The cell product of the present invention can provide repair and regeneration of injured blood vessels in patients with vascular disorders.

The present invention will be described in detail with reference to examples below, but is not limited to the examples in any way.

EXAMPLES

Example 1

Production of Mouse Model of Aneurysm

Experimental protocols using mice in this Example complied with the "Regulations for Animal Experiments and Related Activities at Tohoku University," and experimental animals were prepared according to the regulations under the supervision of the Laboratory Animal Research Center at Tohoku University. More specifically, with reference to a Non-patent Document: Bi Y, et al., PLoS ONE 2013. "Rabbit AAA Model via Periaortic $CaCl_2$ and Elastase Incubation," the model mice were prepared by the following procedures.

Eight-week-old male SCID mice (CLEA Japan) were anesthetized with isoflurane inhalation (induction: 4%, maintenance: 1-1.5%). After opening the abdomen, a region from just below the left renal vein to the aortic bifurcation was circumferentially detached under a stereoscopic microscope (Leica MZ 6). When one or two lumbar artery branches were observed, they were ligated with 10-0 nylon thread and cut off. The periphery of the detached artery was covered with a gauze piece (4×8 mm) immersed in an immersion solution (50 μL of physiological saline containing 0.5 unit/μL of elastase and 0.5 mol/L of $CaCl_2$). After 20 minutes the gauze was removed and the region was washed twice with physiological saline. The control group (Sham group) was treated with a gauze piece containing physiological saline. The mouse thus prepared was used as a mouse model of aneurysm for the following experiments.

Example 2

Preparation of Human Muse Cell

Muse cells were obtained according to the method described in WO2011/007900 on isolation and identification of human Muse cells. A commercially available mesenchymal stem cell (MSC, Lonza) was used as a source of Muse cell. Muse cells used for transplantation expressed green fluorescent protein (GFP) to confirm engraftment to aortic tissues. For cell labeling with GFP, the lentivirus-GFP gene was introduced into the Muse cells in advance. Muse cells labeled with GFP were isolated as a cell double-positive for GFP and SSEA-3 by FACS. The cells remaining after separating Muse cells from MSC were used as non-Muse cells. GFP-positive MSCs were also isolated by FACS and used as MSC group.

Example 3

Administration of Cells to Aneurysm Model Mouse

The aneurysm model mice prepared in Example 1 were divided into 4 groups, and Muse cells ($2\times10^4$, 200 μL) (M), non-Muse cells ($2\times10^4$, 200 μL) (N), MSCs ($2\times10^4$, 200 μL) (MSC) or vehicle (phosphate buffer) (V) was administered to mice in each group intravenously via their tail vein 3 times, at day 3, 10, and 17 after the model preparation. Single-dose groups receiving Muse cells ($2\times10^4$, 200 μL) or non-Muse cells ($2\times10^4$, 200 μL) only at day 3 after the model preparation (M' and N', respectively) were also provided. In addition, a group in which aneurysm was not established was used as Sham group (S) for comparison. The number of animals per group was 8 (but, 11 for the 3-time administration models in the Muse and non-Muse groups, and 4 in the Sham group).

Example 4

Macroscopy of Aneurysm

At week 8 after the preparation of the aneurysm model, the animals were euthanized by oversedation from isoflurane, and their aortae were observed macroscopically. As shown in FIG. 1, the Vehicle group had a markedly expanded artery as compared with the Sham group, indicating that an aortic aneurysm was formed in the Vehicle group. In the Muse cell group, the artery showed little or no expansion as compared with the Vehicle group, and was similar in appearance to that of the Sham group. Artery expansions were observed in the non-Muse cell group and the MSC group although the degrees were less than that in the Vehicle group.

Example 5

Measurement of Aortic Aneurysm Diameter Under a Microscope

The aortic aneurysm diameter was measured under a stereoscopic microscope (Leica MZ6) equipped with a digital camera for microscope (Leica MC120 HD). The aneurysm diameter was evaluated based on the following ratio:

(aneurysm diameter at dissection−aneurysm diameter before model preparation)/aneurysm diameter before model preparation.

Figure 2:
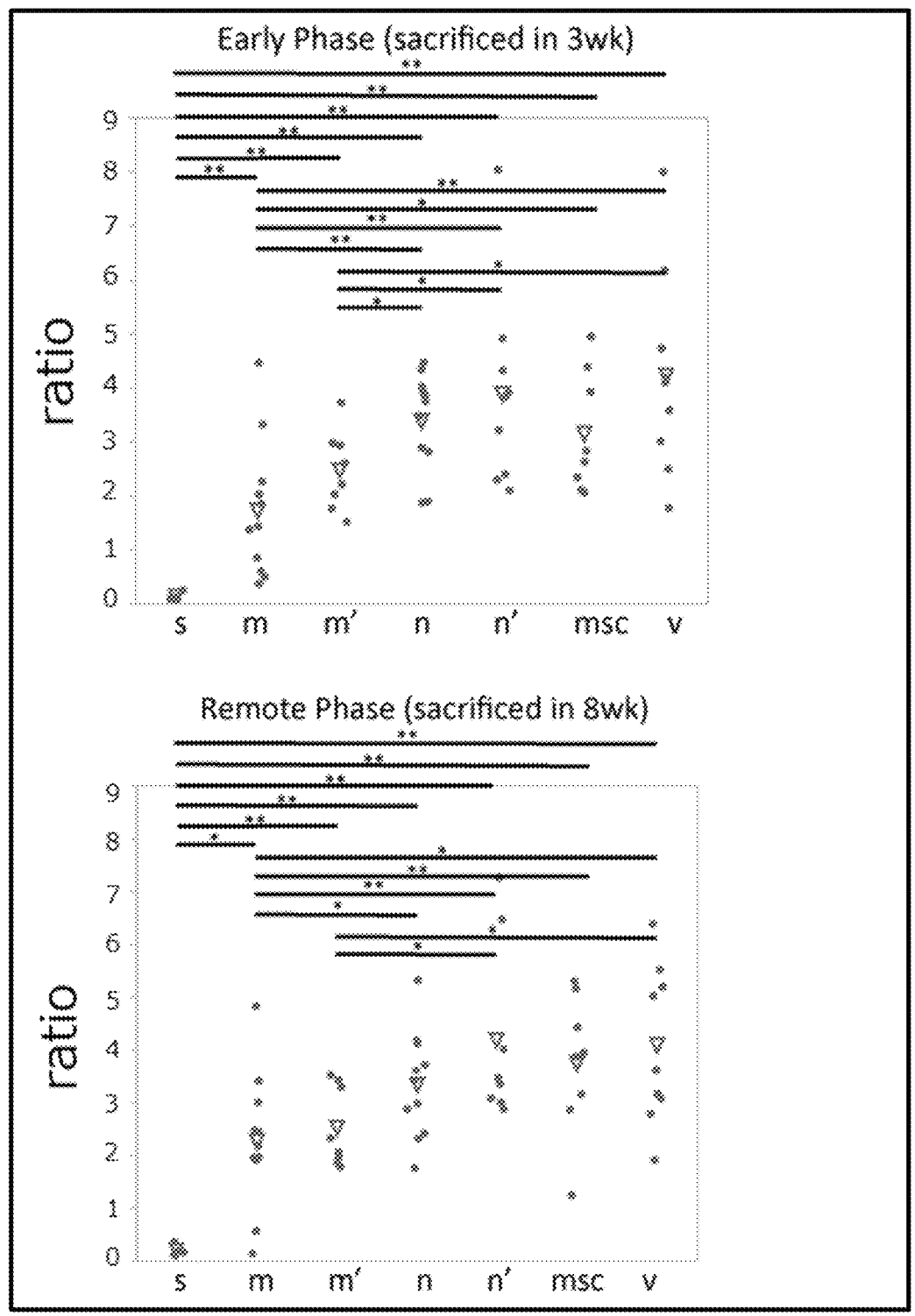
FIG. 2 shows graphs of the aortic aneurysm diameters of the indicated groups after 3 weeks and 8 weeks, as measured by microscopy. * represents $P<0.05$, and ** represents $P<0.01$.

As shown in FIG. 2, at 3 weeks after the model preparation (early phase), both the 3-dose group and the single-dose group of the Muse cell group showed statistically significantly smaller aneurysm diameter as compared with the Vehicle group. On the other hand, there was no significant difference between the Vehicle group and the non-Muse cell and MSC groups. Similarly, even at 8 weeks after the model preparation (remote phase), both the 3-dose group and the single-dose group of the Muse cell group showed statistically significantly smaller aneurysm diameter as compared with the Vehicle group, and there was no significant difference between the Vehicle group and the non-Muse cell and MSC groups. These results showed that three or single administration of Muse cells decreased aneurysm diameter.

Example 6

Ultrasonic Determination of Aneurysm Diameter Over Time

Figure 3:
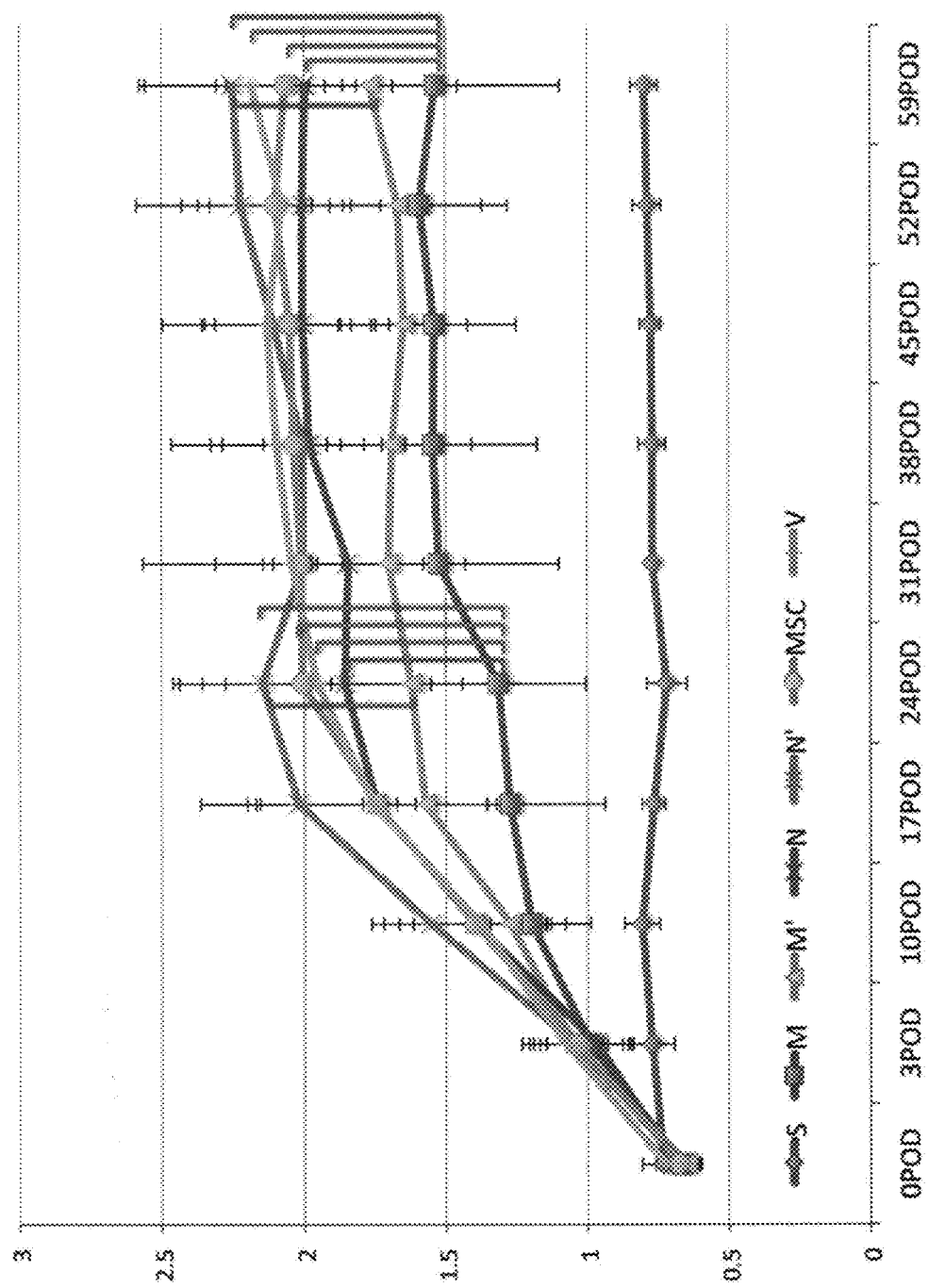
FIG. 3 shows a graph of the aortic aneurysm diameters of the mice of the indicated groups, as measured by ultrasonic determination. The vertical axis shows the aortic aneurysm diameter (mm).

At days 3, 10, 17, 24, 31, 38, 45, 52 and 59 after the cell administration, the aneurysm diameter was measured over time using Ultrasonic imaging device for small animals (SonoScape S6V). As shown in FIG. 3, from day 10 the three-dose and single-dose groups of the Muse cell group tended to show smaller aneurysm diameters, and at days 24 and 52 statistically significant differences were observed as compared with the Vehicle group. On the other hand, there was no statistically significant difference between the Vehicle group and the non-Muse cell and MSC groups. These results showed that three or single administration of Muse cells decreased aneurysm diameter.

Example 7

Histopathological Evaluation of Aortic Elastica

Figure 4:
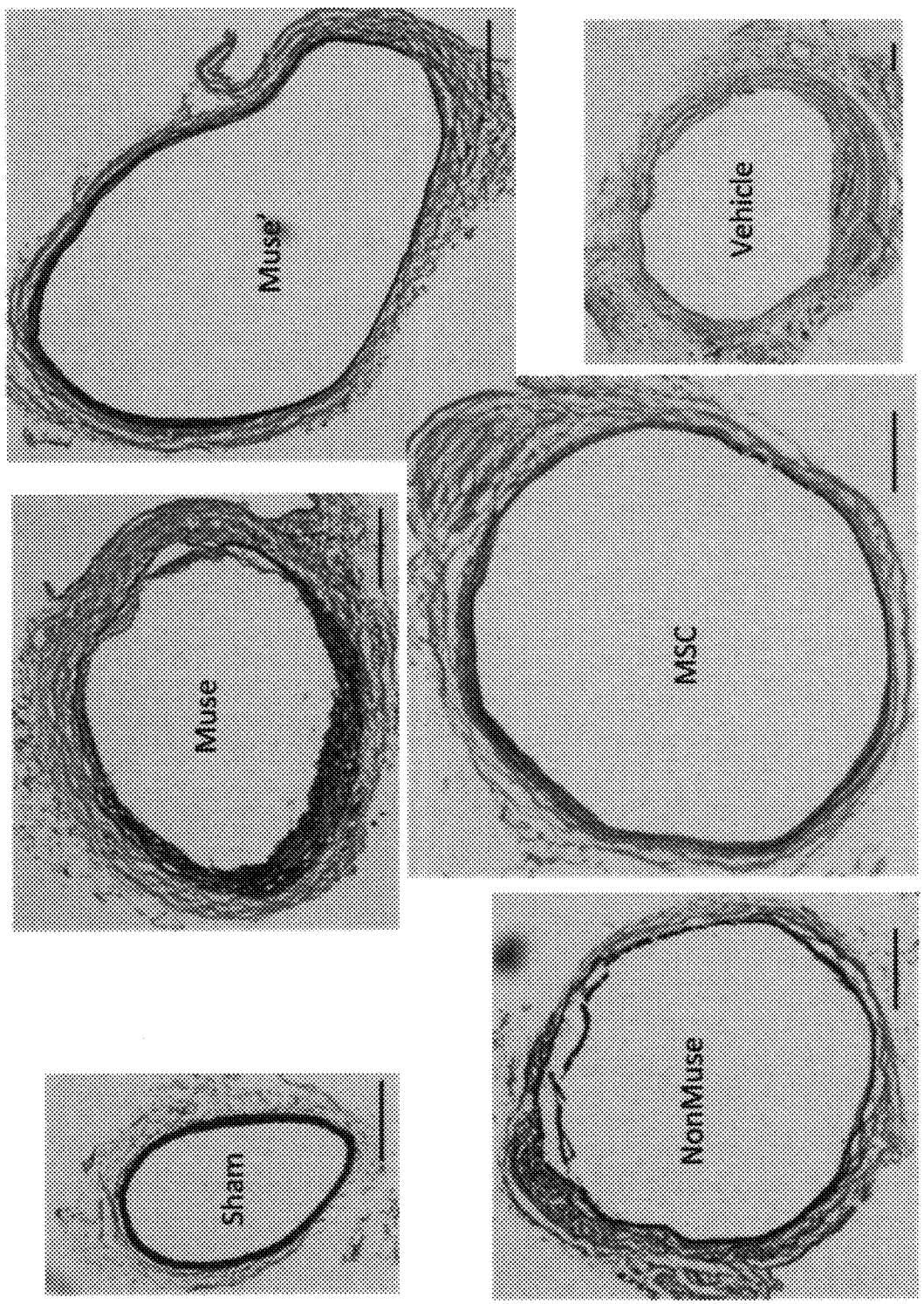
FIG. 4 shows micrographs of Elastica-Masson staining of aortic aneurysm tissues from the mice of the indicated groups after 3 weeks. The scale bars represent 200 μm.
Figure 5:
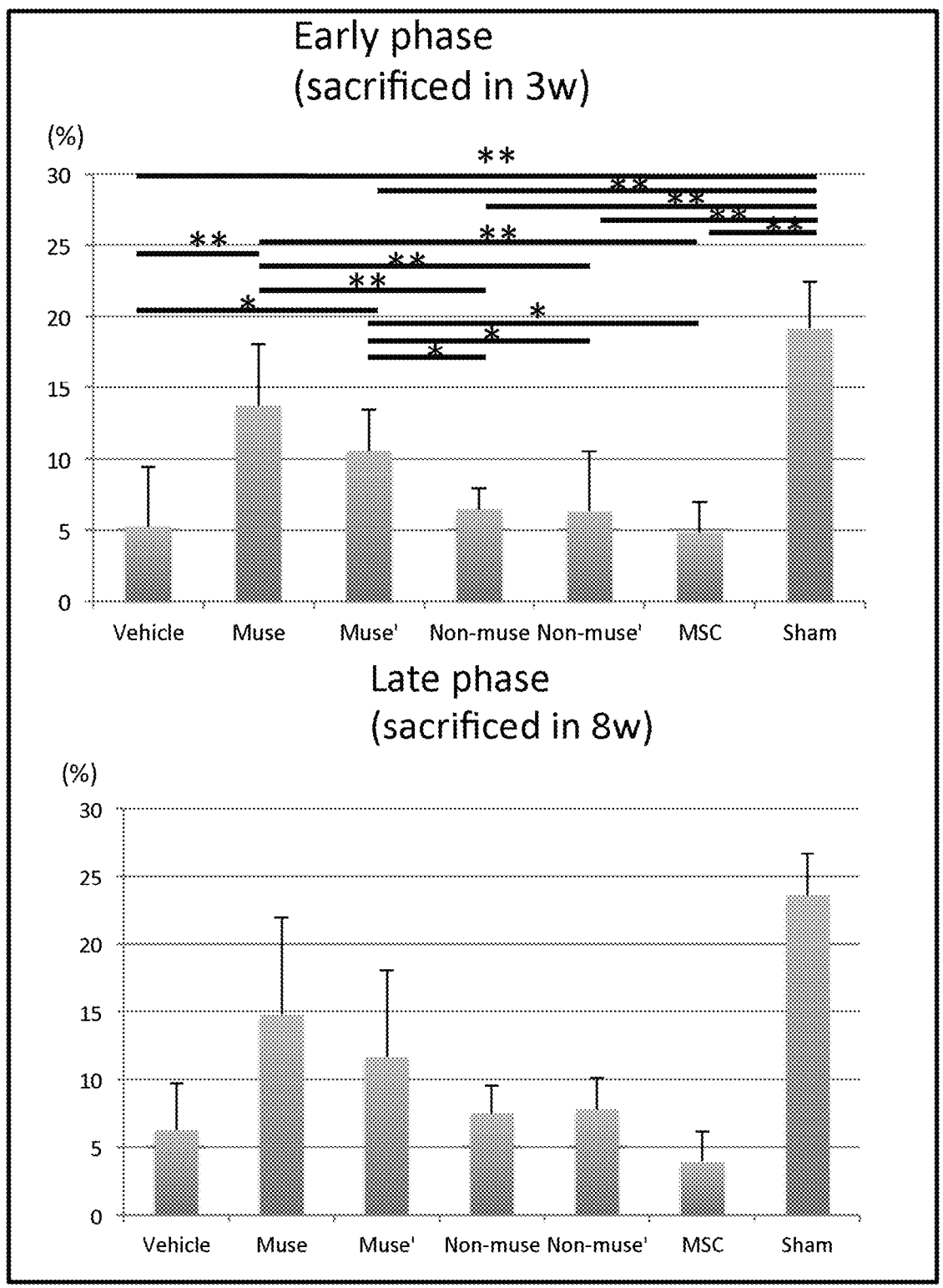
FIG. 5 shows graphs of elastic fiber (Elastin) area quantification results, represented as the ratio of the elastic fiber area to the total vascular wall cross-sectional area of the indicated groups after 3 weeks and after 8 weeks. * represents P<0.05, and ** represents P<0.01.

At 3 or 8 weeks after the model preparation, aortae were fixed with 4% paraformaldehyde (PFA). After frozen sections of the aortae were prepared, they were subjected to Elastica-Masson staining and then observed. As shown in FIG. 4, at 3 weeks after the cell administration, the wavelike elastica structure of the Muse cell group tended to be maintained as compared with the non-Muse group, the MSC group, and the Vehicle group. In FIG. 5, for quantification of elastic fiber (Elastin) area, the ratio of the elastic fiber area to the total vessel wall cross-sectional area was determined. At 3 weeks after the cell administration, the elastic fiber area was significantly decreased in the Vehicle group as compared with the Sham group. In both the 3-dose group and the single-dose group of the Muse cell group, the elastic fiber areas maintained were significantly larger than that of the Vehicle group. On the other hand, no such effect was observed in the non-Muse cell group and the MSC group. Even at 8 weeks after the cell administration, in both the 3-dose group and the single-dose group of the Muse cell group, the elastic fiber areas maintained were significantly larger than that of the Vehicle group. On the other hand, no such effect was observed in the non-Muse cell group and the MSC group. These results showed that Muse cell administration resulted in retention of elastic fibers in the aorta.

Example 8

Differentiation of Muse Cells into Vascular Smooth Muscle

Figure 6:
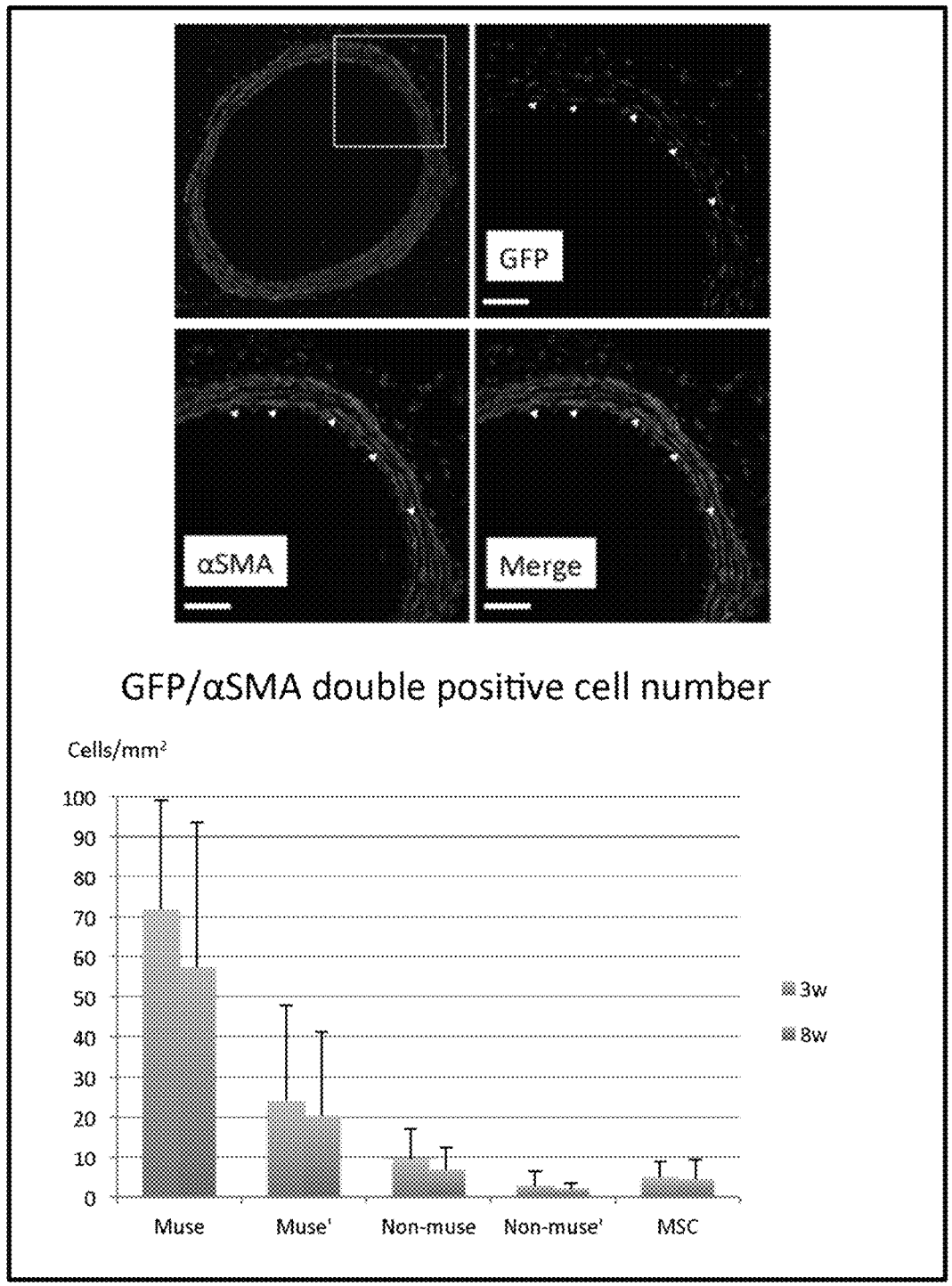
FIG. 6 shows micrographs of immunostaining for alpha-smooth muscle actin (aSMA)/GFP 3 weeks after administration of Muse cells (the scale bars represent 50 μm) (top).

Differentiation of Muse cells into vascular smooth muscle was evaluated using aortic preparations at 3 or 8 weeks after the cell administration. Aortae fixed with 4% PFA were immunohistochemically stained with mouse anti-αSMA antibody (Thermo, diluted in 1:200) and rabbit anti-GFP antibody (Abcam, diluted in 1:500) as primary antibodies; and then donkey anti-mouse IgG antibody (Life Technology, diluted in 1:500) and donkey anti-rabbit IgG antibody (Life Technology, diluted in 1:500) as secondary antibodies. As shown in the images in FIG. 6 (top), at 3 weeks after the Muse cell administration, cytoplasm of vascular smooth muscle cells expressing αSMA was stained in red, while cytoplasm of Muse cells expressing GFP was stained in green. As shown in the merged image, cells stained for both αSMA and GFP were observed, which confirmed that the administered Muse cells differentiated into vascular smooth muscle. The graph in FIG. 6 (bottom) shows the number of αSMA/GFP double-positive cells per unit area in each group. In the Muse cell group, double-positive cells were observed most frequently at 3 and 8 weeks after the cell administration in the 3-dose group, and also observed in the single-dose group. On the other hand, only few double-positive cells were observed in the non-Muse cell group and the MSC group.

Example 9

Differentiation of Muse Cells into Vascular Endothelial Cell

Figure 7:
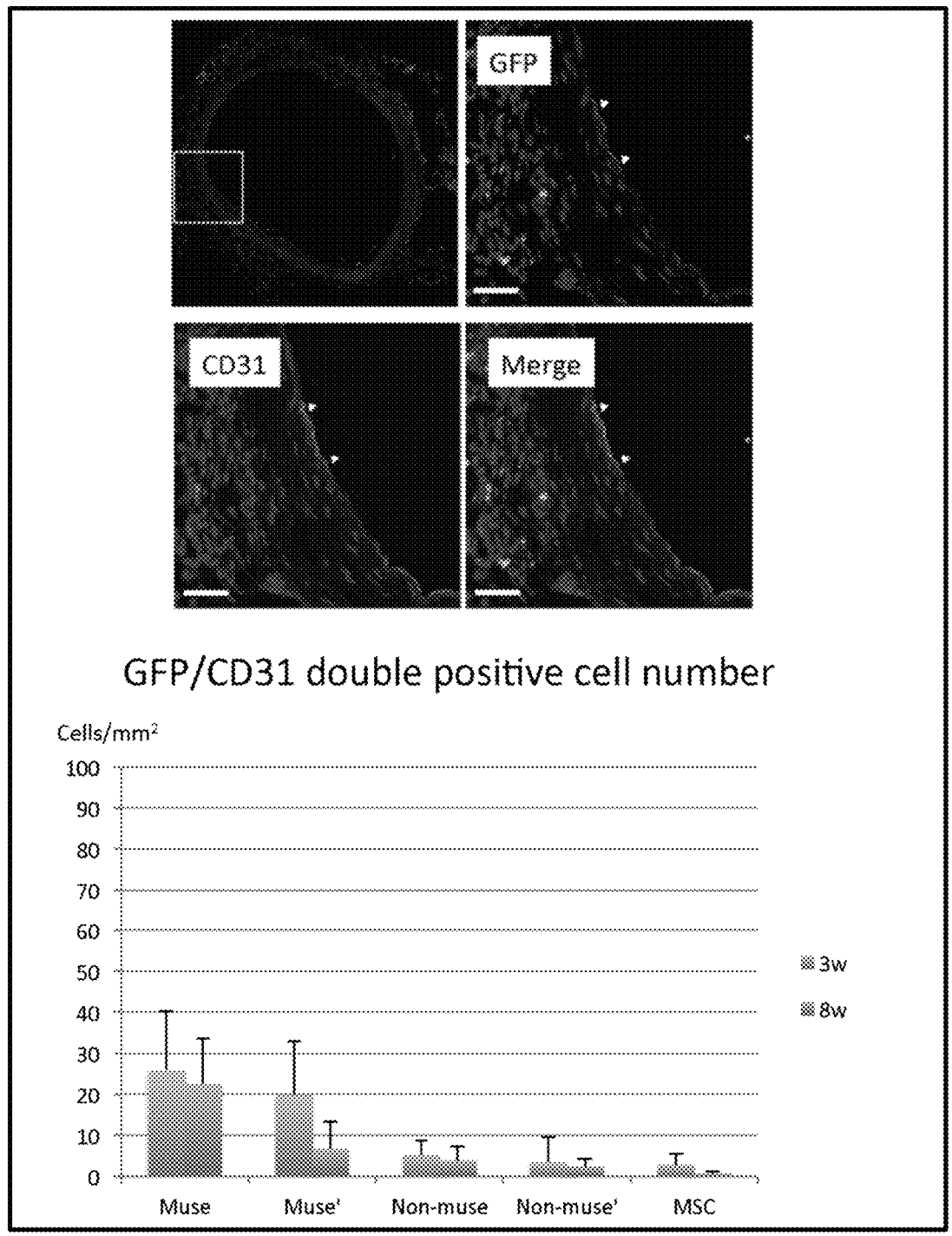
FIG. 7 shows micrographs of immunostaining for CD31/GFP 3 weeks after administration of Muse cells (the scale bars represent 50 μm) (top).

Differentiation of Muse cells into vascular endothelial cell was evaluated using aortic preparations at 3 or 8 weeks after the cell administration. Aortae fixed with 4% PFA were stained with goat anti-CD31 antibody (Santa Cruz, diluted in 1:50) or rabbit anti-GFP antibody (Abcam, diluted in 1:200) as primary antibodies; and then donkey anti-goat IgG antibody (Life Technology, diluted in 1:500) or donkey anti-rabbit IgG antibody (Life Technology, diluted in 1:500) as secondary antibodies. As shown in the images in FIG. 7 (top), at 3 weeks after the Muse cell administration, cytoplasm of vascular endothelial cells expressing CD31 was stained in red, while cytoplasm of Muse cells expressing GFP was stained in green. As shown in the merged image, cells stained for both CD31 and GFP were observed, which confirmed that the administered Muse cells differentiated into vascular endothelial cells. The graph in FIG. 7 (bottom) shows the number of CD31/GFP double-positive cells per unit area. In the Muse cell group, double-positive cells were observed most frequently at 3 and 8 weeks after the cell administration in the 3-dose group, and also observed in the single-dose group. On the other hand, only few double-positive cells were observed in the non-Muse cell group and the MSC group.

Example 10

Migration of Macrophage to Aorta

Figure 8:
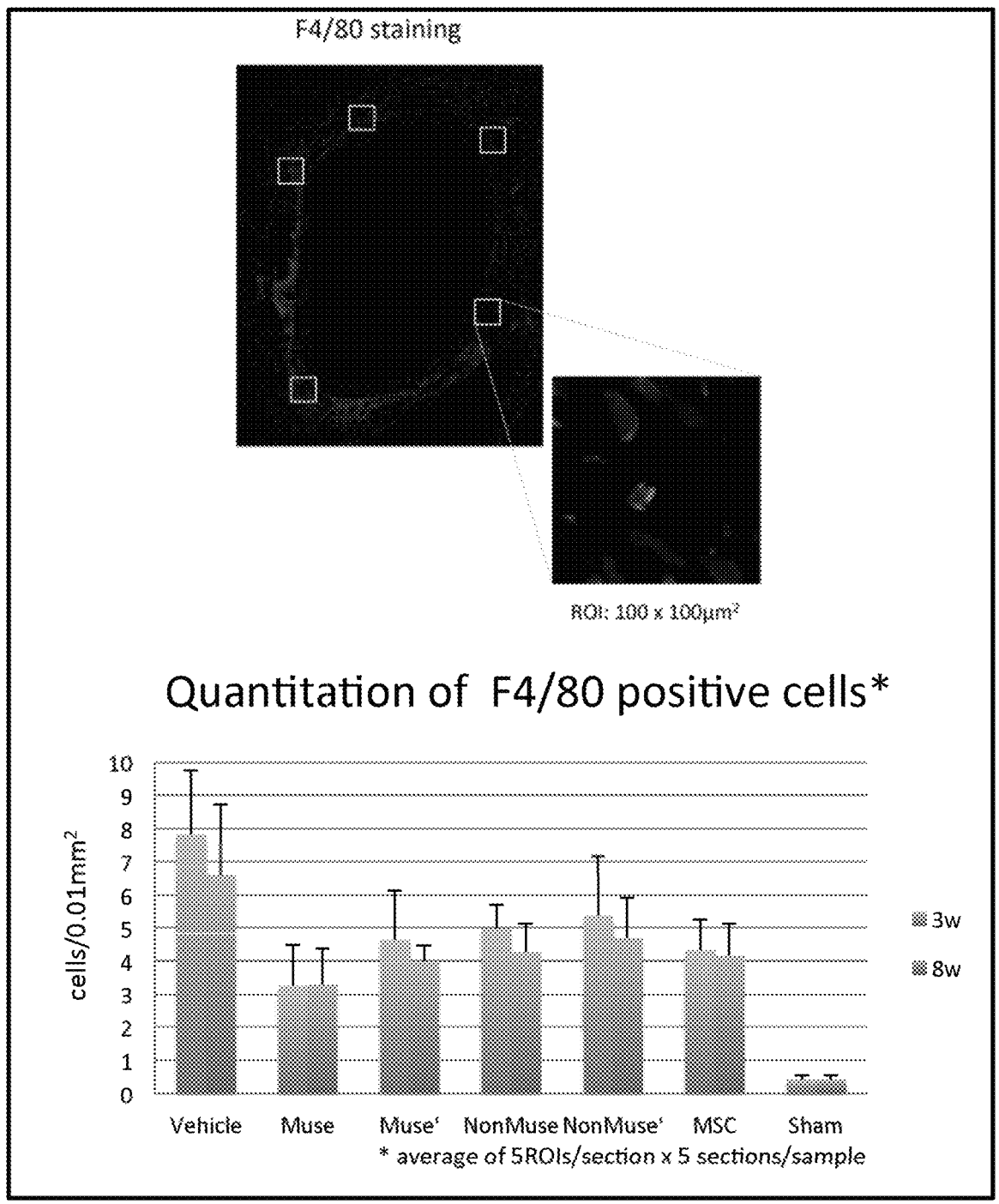
FIG. 8 shows micrographs of immunostaining for F4/80 3 weeks after administration of Muse cells (top).

Detection of macrophages was carried out using aortic preparations at 3 or 8 weeks after the cell administration. Rat anti-F4/80 antibody (AbD, diluted in 1:100) as a primary antibody and goat anti-rat antibody (Life Technology, diluted in 1:500) as a secondary antibody were used. As shown in FIG. 8, cells with cytoplasm stained in red were identified as macrophage. More macrophages were detected in the vehicle group at both 3 and 8 weeks after the cell administration as compared with the Sham group. Less macrophages were detected in the 3-dose group for Muse cell at both 3 and 8 weeks after the cell administration, suggesting that inflammatory cell infiltration associated with vascular injury was suppressed. Although not as much as the decrease observed in the 3-dose group with Muse cell, decreases in number of macrophages were observed in other cell administration groups.

Example 11

Determination of Cell Division in Muse Cells

Figure 9:
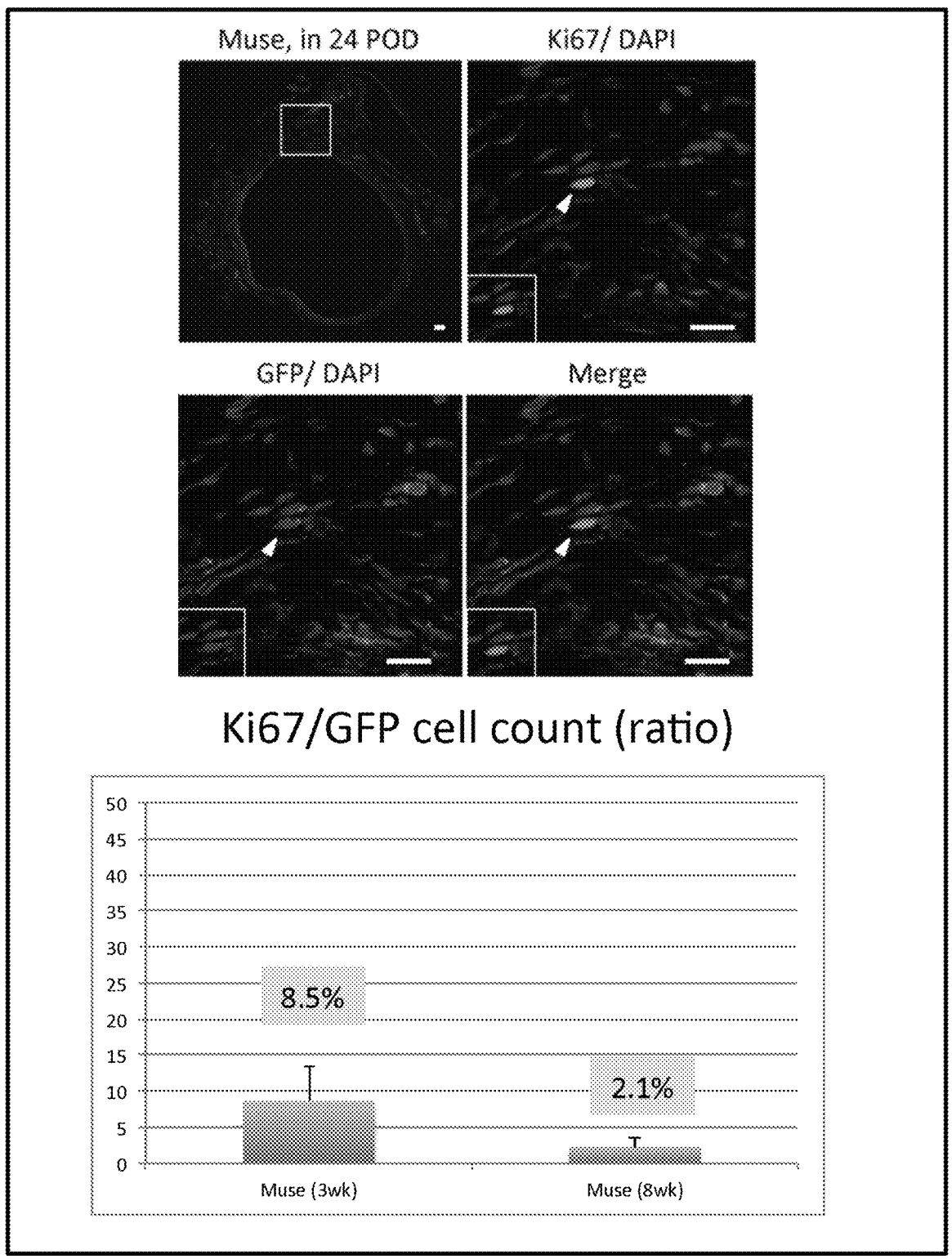
FIG. 9 shows micrographs of immunostaining for Ki67/GFP 3 weeks after administration of Muse cells (the scale bars represent 50 μm) (top).

Whether Muse cells engrafted to aorta were dividing was determined using aortic preparations at 3 or 8 weeks after the cell administration. Rabbit anti-Ki67 antibody (Thermo, diluted in 1:100) and goat anti-GFP antibody (Abcam, diluted in 1:1000) as primary antibodies; donkey anti-rabbit antibody (Life Technology, diluted in 1:500) and donkey anti-goat antibody (Life Technology, diluted in 1:500) as secondary antibodies were used. As shown in FIG. 9, since nuclei of dividing cells were stained in red, nuclei of dividing Muse cells were stained in red and cytoplasms thereof were stained in green. About 8.5% of the Muse cells were dividing at 3 weeks after the cell administration, indicating that a part of the Muse cells engrafted to tissues proliferated by cell division. However, at 8 weeks after the cell administration, Muse cells showing cell division decreased to about 2.1%, indicating that the engrafted Muse cells gradually shift to differentiation. This suggested that Muse cells exerted their therapeutic effects through migration, proliferation and differentiation in the early phase, and then gradually ended the proliferation, thereby acting at the injured site without becoming malignant.

Example 12

Distribution of Muse Cells and Non-Muse Cells

Figure 10:
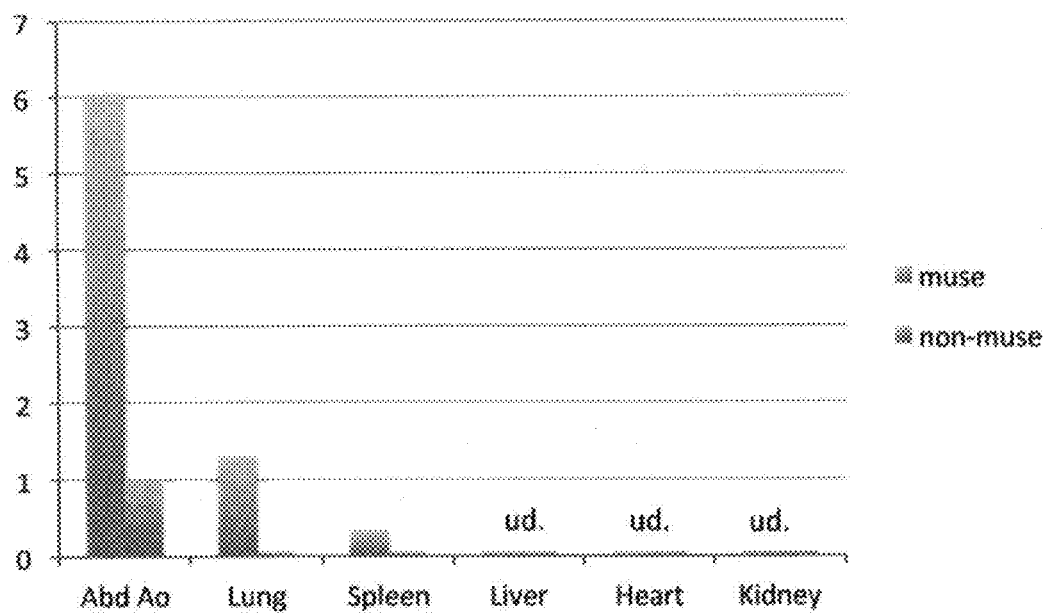
FIG. 10 is a graph showing the Alu sequence detection results in the indicated organs of the Muse cell-treated group and the non-Muse cell-treated group after 8 weeks. The concentrations of Alu sequence detected in the other organs and the Muse cell-treated group are expressed as ratios to that derived from the aorta in the non-muse cell-treated group, which is considered as 1.

Distribution of Muse cells or non-Muse cells at 8 weeks after the cell administration was investigated by real-time PCR targeting Alu sequence specific for human DNA. The results are shown in FIG. 10. Muse cells were also found in the lung, but most of the Muse cells were distributed in the aortic aneurysm site (Abd Ao).

Example 13

Analysis of Differentiation Potential of Muse Cells into Various Vascular Cells and Stress Tolerance of Muse Cells Differentiation potential of human Muse cells into various vascular cells and stress tolerance of Muse cells were investigated by marker expression analysis using quantitative PCR. As controls, endothelial precursor cells (EPC) that are known to differentiate into endothelial cells and CD34$^+$ progenitor cells (including hematopoietic stem cells and vascular progenitor cells) that are known to differentiate into endothelial cells and vascular smooth muscle cells were used. The Muse cells were cultured in the presence of serum derived from a severe combined immunodeficient (SCID) mouse in which aneurysm was induced (at postoperative day 3).

Figure 11:
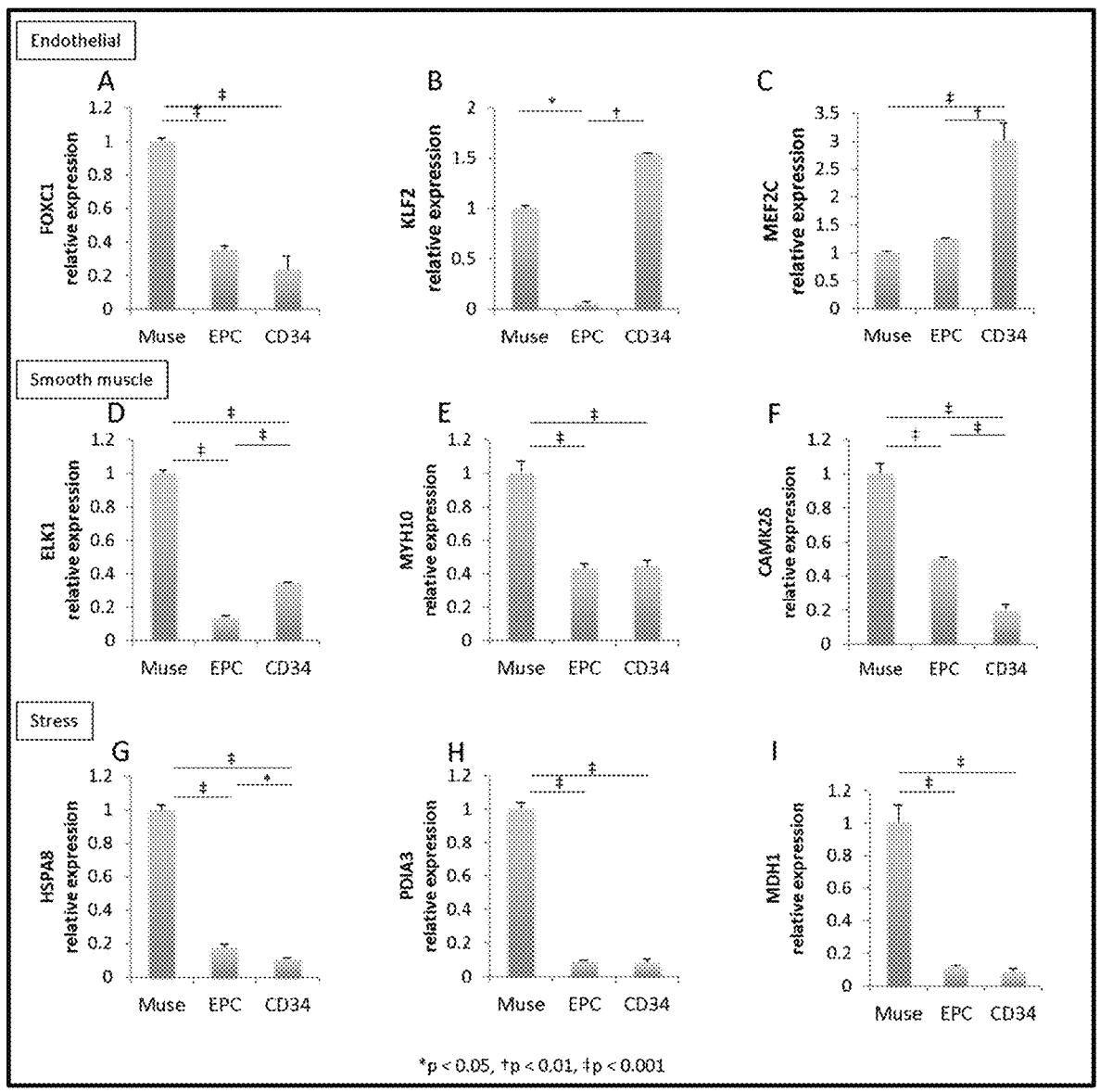
FIG. 11 shows expression of early endothelial cell markers (A to C), dedifferentiated smooth muscle cell markers (D to F), and stress tolerance-related markers (G to I) in human Muse cell, endothelial precursor cell (EPC), and CD34$^+$ progenitor cell, as analyzed by quantitative PCR. Each expression level is indicated as relative expression level normalized by the expression level of β-actin.

The results are shown in FIG. 11.

Among the epithelial markers, FOXC1 was most highly expressed in Muse cells (each $p<0.001$ for EPC and CD34$^+$ cell). On the other hand, KLF2 was most highly expressed in CD34$^+$ cells ($p<0.01$ for EPC, $p=0.34$ for Muse), and MEF2C was also most highly expressed in CD34$^+$ cells ($p<0.01$ for EPC, $p<0.001$ for Muse). Expressions of KLF2 and MEF2C in Muse cells were moderate.

Expressions of ELK1, MYH10 and CAMK2δ, markers for dedifferentiated vascular smooth muscle cell, were highest in Muse cells (each $p<0.001$ for EPC and CD34$^+$ cells).

Expressions of HSPA8, PDIA3 and MDH1, factors involved in stress tolerance, were markedly high in Muse cells (each p<0.001 for EPC and CD34+ cells).

These results showed that Muse cells had the ability to differentiate into endothelial cells and vascular smooth muscle cells and were highly tolerant to stress.

Example 14

Kinetic Analysis of Muse Cells in an In Vitro Aneurysm Model

Figure 12A:
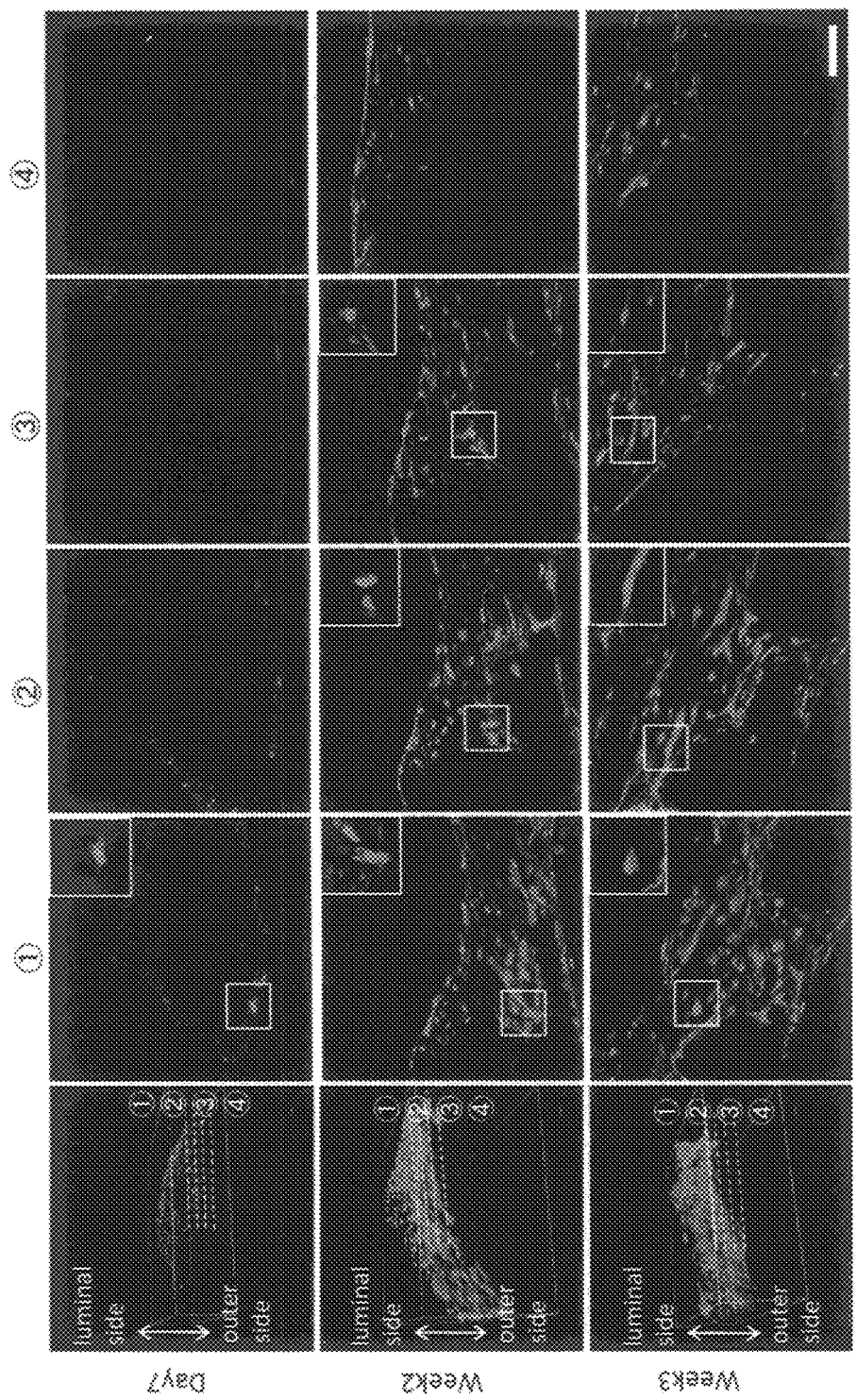
FIG. 12A shows representative multiphoton laser micrographs (photography) of mouse aneurysm co-cultured with Muse cells. The left column depicts 3D reconstruction images of artery samples showing the positions of the images in the indicated axial direction (broken lines 1 to 4) captured every 20 μm from the luminal side to the outer side. The scale bar represents 100 μm.
Figure 12B:
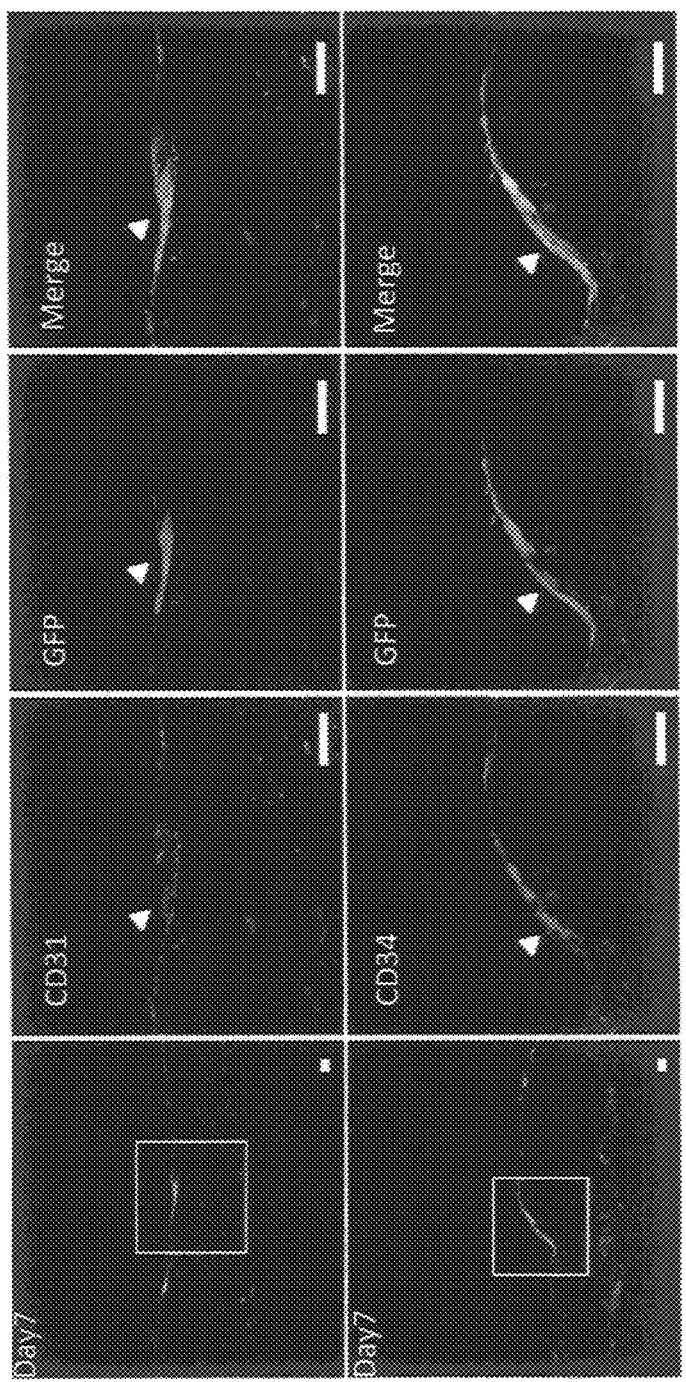
FIG. 12B shows representative sagittal sections (photographs) of frozen sections stained with CD31 or CD34. The arrowheads indicate cells that are also positive for GFP. The scale bars represent 50 μm.

In order to determine whether Muse cells possess differentiation potential under an aneurysmal microenvironment, human Muse cells and aneurysm tissues were co-cultured. Specifically, based on the method described in J Vasc Surg. 2015; 62:1054-1063, the abdominal aorta of an immunodeficient mouse (SCID) was wrapped with a gauze immersed in 0.5 mol/L $CaCl_2$ solution containing porcine pancreatic elastase (0.5 unit/μl) and incubated for about 20 minutes to prepare an abdominal aneurysm model. The aneurysm tissue was excised, cut longitudinally and spread, placed on a culture dish with the luminal side of the artery facing upwards, and then 10,000 GFP+ Muse cells were added. As shown in FIG. 12A, at Day 7 Muse cells were localized only in the tunica intima that is the surface layer of the aneurysm wall, but at Weeks 2 and 3 Muse cells invaded into the arterial tissue and were also found in the tunica media and the inner layer of the tunica adventitia. In the immunostaining at Day 7, as shown in FIG. 12B, Muse cells (labeled with GFP) present in the tunica intima were observed as cells positive for CD31 and CD34, markers for vascular endothelial cells.

Example 15

Kinetic Analysis of Muse Cells in an In Vivo Model

In order to determine whether Muse cells migrate and bind to aneurysm tissues, aneurysm model mice were administered intravenously with 20,000 GFP+ Muse cells and dissected at Days 3 and 5 after the administration. Then, the Muse cell migration kinetics were analyzed with a multiphoton laser microscope.

Figure 13A:
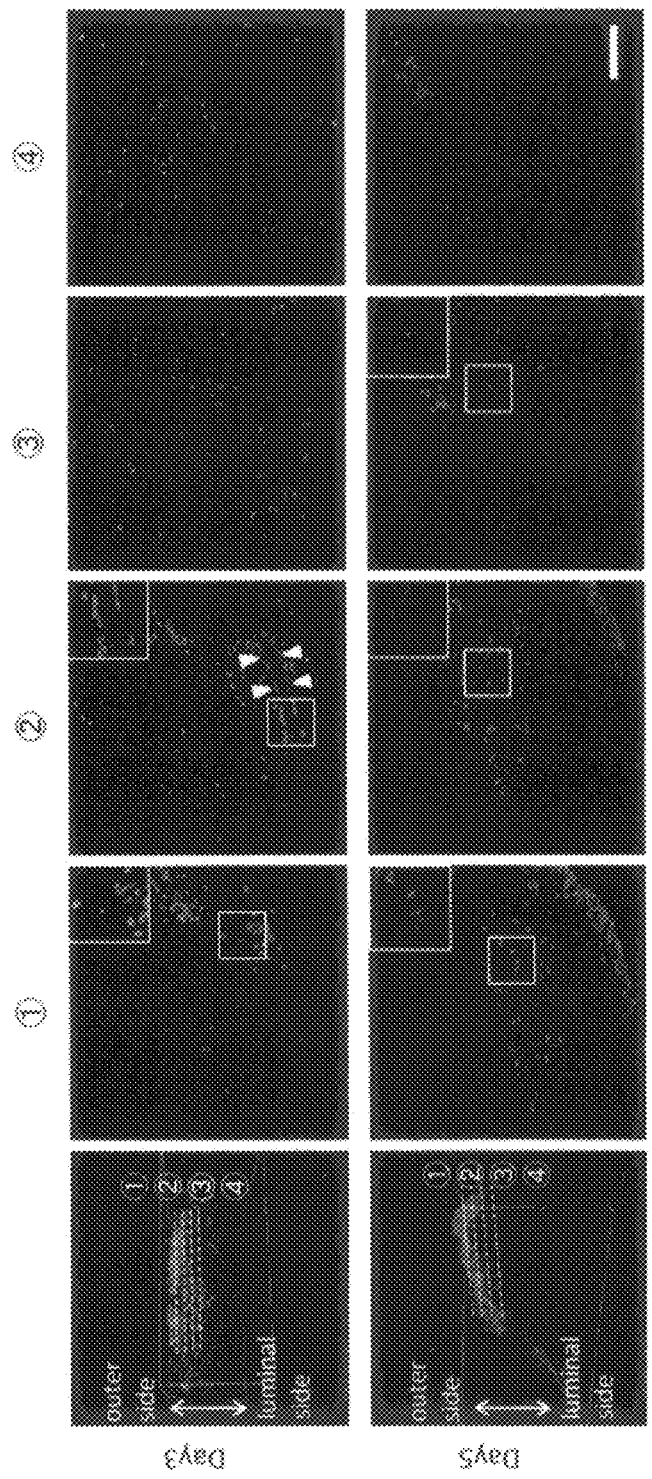
FIG. 13A shows representative multiphoton laser micrographs (photography) of aneurysms obtained at Days 3 and 5 in an in vivo aneurysm model treated with Muse cells. The left column depicts 3D reconstruction images of artery samples showing the positions of the images in the indicated axial direction (broken lines 1 to 4) captured every 20 μm from the luminal side to the outer side. The scale bar represents 100 μm.
Figure 13B:
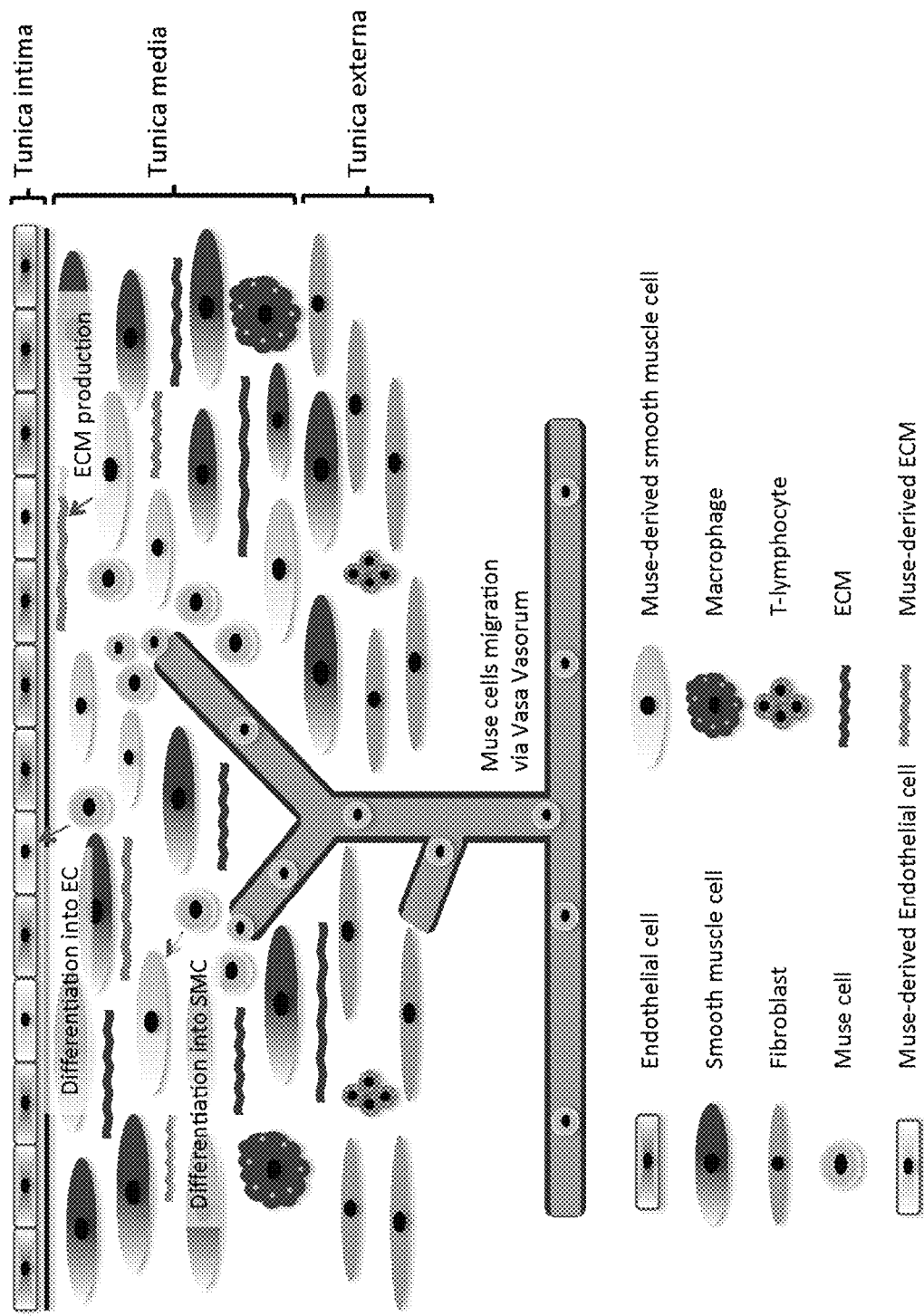
FIG. 13B shows a schematic of aneurysm treatment with Muse cell.

Unlike the in vitro co-culture experiment of Example 14 in which Muse cells first adhered to the luminal side of the aneurysm and gradually invaded deeper into the tunica media and tunica adventitia layers, as shown in FIG. 13A, at Day 3, GFP+ Muse cells were detected only in the tunica adventitia of the vascular system, some of which accumulated around the "vasa vasorum" in the tunica adventitia (arrow). At Day 5, the GFP+ Muse cells remained in the tunica adventitia, proliferating towards the tunica media and tunica intima. These results suggested that unlike in the in vitro model, Muse cells that were intravenously administered invaded into aneurysm tissues not from the luminal side of the vessel but via "vasa vasorum" in the tunica adventitia, and then migrated towards the tunica media and tunica intima (FIG. 13B).

INDUSTRIAL AVAILABILITY

The cell product of the present invention can reconstruct and repair tissues in injured sites, as well as recover their functions when it is administered to patients with vascular disorders, and thus can be applied to prevention and treatment of vascular disorders.

The invention claimed is:

1. A method for treating an aortic aneurysm in a human, the method comprising:
   isolating human pluripotent stem cells from mesenchymal tissue; and
   intravenously administering the pluripotent stem cells to a human that has an aortic aneurysm,
   wherein the pluripotent stem cells are positive for SSEA-3, which are isolated by using an antigen marker SSEA-3 as an index, or the pluripotent stem cells are concentrated by external stress treatment,
   wherein the pluripotent stem cell has the following characteristics:
   (i) expressing SSEA-3-positivity
   (ii) having low or no telomerase activity;
   (iii) capable of differentiating into any of tridermic cells;
   (iv) showing no neoplastic proliferation; and
   (v) having self-renewal capacities.

2. The method of claim 1, wherein the method treats an aortic aneurysm in the human, wherein the aortic aneurysm is abdominal aortic aneurysm or thoracic aortic aneurysm.

* * * * *

UNITED STATES PATENT AND TRADEMARK OFFICE
CERTIFICATE OF CORRECTION

PATENT NO. : 11,419,899 B2
APPLICATION NO. : 16/321203
DATED : August 23, 2022
INVENTOR(S) : Yoshikatsu Saiki et al.

It is certified that error appears in the above-identified patent and that said Letters Patent is hereby corrected as shown below:

In the Claims

In Column 16, Claim 1, Line 27, delete "isolating" and insert -- i) isolating --.

In Column 16, Claim 1, Line 29, delete "intravenously" and insert -- ii) intravenously --.

In Column 16, Claim 1, Line 31-34, delete "wherein the pluripotent stem cells are positive for SSEA-3. which are isolated by using an antigen marker SSEA-3 as an index, or the pluripotent stem cells are concentrated by external stress treatment,".

In Column 16, Claim 2, Line 42-43, delete "wherein the method treats an aortic aneurysm in the human, wherein the aortic aneurysm" and insert -- wherein the aortic aneurysm --.

In Column 16, Claim 2, Line 44, delete "is abdominal aortic aneurysm or thoracic aortic aneurysm" and insert -- is an abdominal aortic aneurysm or a thoracic aortic aneurysm --.

Signed and Sealed this
Nineteenth Day of December, 2023

Katherine Kelly Vidal
*Director of the United States Patent and Trademark Office*